United States Patent
Zambon et al.

(10) Patent No.: US 9,708,317 B2
(45) Date of Patent: Jul. 18, 2017

(54) PROCESS FOR THE PREPARATION OF 8-(4-AMINOPHENOXY)-4H-PYRIDO[2,3-B]PYRAZIN-3-ONE DERIVATIVES

(71) Applicants: CANCER RESEARCH TECHNOLOGY LIMITED, London (GB); INSTITUTE OF CANCER RESEARCH: ROYAL CANCER HOSPITAL (THE), London (GB)

(72) Inventors: Alfonso Zambon, Sutton (GB); Dan Niculescu-Duvaz, Sutton (GB); Richard Chubb, Sunderland (GB); Caroline Joy Springer, Sutton (GB)

(73) Assignees: Cancer Research Technology Limited, London (GB); Oxy Scientific Limited, Sunderland (GB); The Institute of Cancer Research: Royal Cancer Hospital, Greater London (GB)

( * ) Notice: Subject to any disclaimer, the term of this patent is extended or adjusted under 35 U.S.C. 154(b) by 0 days.

(21) Appl. No.: 15/038,337

(22) PCT Filed: Nov. 25, 2014

(86) PCT No.: PCT/GB2014/053489
§ 371 (c)(1),
(2) Date: May 20, 2016

(87) PCT Pub. No.: WO2015/075482
PCT Pub. Date: May 28, 2015

(65) Prior Publication Data
US 2016/0297814 A1    Oct. 13, 2016

(30) Foreign Application Priority Data
Nov. 25, 2013 (GB) .................................. 1320732.9

(51) Int. Cl.
*C07D 471/04* (2006.01)

(52) U.S. Cl.
CPC .................................. *C07D 471/04* (2013.01)

(58) Field of Classification Search
CPC .................................................. C07D 471/04
See application file for complete search history.

(56) References Cited

U.S. PATENT DOCUMENTS

| 4,082,845 A | 4/1978 | Saari et al. |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,521,073 A | 5/1996 | Davis et al. |
| 5,877,020 A | 3/1999 | Alitalo et al. |
| 5,879,672 A | 3/1999 | Davis et al. |
| 5,882,864 A | 3/1999 | An et al. |

(Continued)

FOREIGN PATENT DOCUMENTS

| CN | 101084217 A | 12/2007 |
| EP | 1724268 A1 | 11/2006 |

(Continued)

OTHER PUBLICATIONS

Abasolo et al., "Kinetic study on the anelation of heterocycles. 2. pyrido[2,3-b]pyrazine and pyrido[3,4-b]pyrazine derivatives synthesized by the Hinsberg reaction," J Heterocyclic Chem. 27(2):157-162 (1990).

Adams et al., "Roles of ephrinB ligands and EphB receptors in cardiovascular development: demarcation of arterial/venous domains, vascular morphogenesis, and sprouting angiogenesis," Genes Dev. 13(3):295-306 (1999).

(Continued)

*Primary Examiner* — Kahsay Habte

(57) ABSTRACT

The present invention pertains generally to the field of organic chemical synthesis, and in particular to certain methods for the synthesis of 8-(4-aminophenyoxy)-4H-pyrido[2,3-b]pyrazin-3-one and related compounds (denoted herein as (3)) from 4-(4-aminophenyoxy)pyridine-2,3-diamine and related compounds (denoted herein as (1)), by reaction with glyoxylic acid (denoted herein as (2)). The compounds (3) are useful in the synthesis of known anticancer agents, such as 1-(5-tert-butyl-2-(4-methyl-phenyl)-pyrazol-3-yl)-3-[2-fluoro-4-[(3-oxo-4H-pyrido[2,3-b]pyrazin-8-yl)oxy]phenyl]urea.

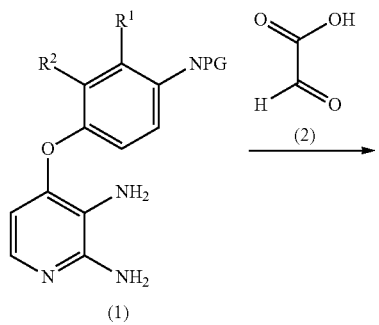

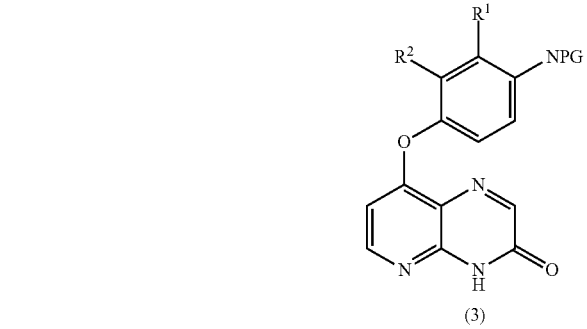

83 Claims, No Drawings

(56) References Cited

U.S. PATENT DOCUMENTS

| | | |
|---|---|---|
| 6,030,831 A | 2/2000 | Godowski et al. |
| 6,218,529 B1 | 4/2001 | An et al. |
| 6,258,809 B1 | 7/2001 | Rajagopalan et al. |
| 6,492,529 B1 | 12/2002 | Kapadia et al. |
| 7,625,922 B2 | 12/2009 | Niculescu-Duvaz et al. |
| 7,951,819 B2 | 5/2011 | Niculescu-Duvaz et al. |
| 8,198,279 B2 | 6/2012 | Springer et al. |
| 8,383,816 B2 | 2/2013 | Niculescu-Duvaz et al. |
| 8,546,387 B2 | 10/2013 | Springer et al. |
| 8,815,896 B2 | 8/2014 | Springer et al. |
| 8,912,191 B2 | 12/2014 | Springer et al. |
| 9,120,789 B2 | 9/2015 | Springer et al. |
| 9,155,737 B2 | 10/2015 | Springer et al. |
| 2004/0082583 A1 | 4/2004 | Cheung et al. |
| 2007/0287838 A1 | 12/2007 | Niculescu-Duvaz et al. |
| 2008/0113967 A1 | 5/2008 | Flynn et al. |
| 2009/0325945 A1 | 12/2009 | Niculescu-Duvaz et al. |
| 2011/0053946 A1 | 3/2011 | Niculescu-Duvaz et al. |
| 2012/0238568 A1 | 9/2012 | Springer et al. |
| 2014/0121212 A1 | 5/2014 | Springer et al. |
| 2014/0357663 A1 | 12/2014 | Springer et al. |
| 2015/0182526 A1 | 7/2015 | Springer et al. |
| 2016/0002230 A1 | 1/2016 | Springer et al. |
| 2016/0030405 A1 | 2/2016 | Springer et al. |

FOREIGN PATENT DOCUMENTS

| | | |
|---|---|---|
| JP | S5665863 A | 6/1981 |
| JP | S5738777 A | 3/1982 |
| NZ | 555005 A | 10/2010 |
| WO | WO-98/13350 A1 | 4/1998 |
| WO | WO-99/16438 A1 | 4/1999 |
| WO | WO-99/21859 A1 | 5/1999 |
| WO | WO-00/35436 A2 | 6/2000 |
| WO | WO-00/40235 A2 | 7/2000 |
| WO | WO-00/45435 A1 | 8/2000 |
| WO | WO-01/05392 A2 | 1/2001 |
| WO | WO-01/36383 A1 | 5/2001 |
| WO | WO-01/46196 A1 | 6/2001 |
| WO | WO-02/102367 A1 | 12/2002 |
| WO | WO-03/056036 A2 | 7/2003 |
| WO | WO-2004/014300 A2 | 2/2004 |
| WO | WO-2004/083458 A1 | 9/2004 |
| WO | WO-2004/110452 A1 | 12/2004 |
| WO | WO-2006/003378 A1 | 1/2006 |
| WO | WO-2006/024834 A1 | 3/2006 |
| WO | WO-2006/040568 A1 | 4/2006 |
| WO | WO-2006/043090 A1 | 4/2006 |
| WO | WO-2006/067466 A2 | 6/2006 |
| WO | WO-2007/059202 A2 | 5/2007 |
| WO | WO-2007/064872 A2 | 6/2007 |
| WO | WO-2007/067444 A1 | 6/2007 |
| WO | WO-2007/076092 A2 | 7/2007 |
| WO | WO-2007/125330 A1 | 11/2007 |
| WO | WO-2008/009700 A1 | 1/2008 |
| WO | WO-2008/044688 A1 | 4/2008 |
| WO | WO-2009/007934 A2 | 1/2009 |
| WO | WO-2009/077766 A1 | 6/2009 |
| WO | WO-2009/130487 A1 | 10/2009 |
| WO | WO-2010/038085 A2 | 4/2010 |
| WO | WO-2010/038086 A2 | 4/2010 |
| WO | WO-2010/067130 A1 | 6/2010 |
| WO | WO-2010/067131 A1 | 6/2010 |
| WO | WO-2010/112936 A1 | 10/2010 |
| WO | WO-2011/004276 A1 | 1/2011 |
| WO | WO-2011/028540 A1 | 3/2011 |
| WO | WO-2011/048111 A1 | 4/2011 |
| WO | WO-2011/070368 A1 | 6/2011 |
| WO | WO-2011/070369 A1 | 6/2011 |
| WO | WO-2011/092469 A1 | 8/2011 |
| WO | WO-2011/121366 A1 | 10/2011 |
| WO | WO-2011/124923 A2 | 10/2011 |
| WO | WO-2011/124930 A1 | 10/2011 |
| WO | WO-2011/158039 A1 | 12/2011 |
| WO | WO-2011/158042 A2 | 12/2011 |
| WO | WO-2011/158044 A2 | 12/2011 |
| WO | WO-2012/008564 A1 | 1/2012 |
| WO | WO-2012/052753 A1 | 4/2012 |
| WO | WO-2012/149547 A1 | 11/2012 |
| WO | WO-2012/177725 A1 | 12/2012 |
| WO | WO-2013/001372 A2 | 1/2013 |
| WO | WO-2013/033133 A1 | 3/2013 |
| WO | WO-2013/050756 A1 | 4/2013 |
| WO | WO-2013/050757 A1 | 4/2013 |
| WO | WO-2014/027209 A1 | 2/2014 |
| WO | WO-2014/033446 A1 | 3/2014 |
| WO | WO-2014/033447 A2 | 3/2014 |
| WO | WO-2014/033448 A1 | 3/2014 |
| WO | WO-2014/033449 A1 | 3/2014 |
| WO | WO-2014/076484 A1 | 5/2014 |
| WO | WO-2014/140582 A1 | 9/2014 |
| WO | WO-2014/140597 A1 | 9/2014 |
| WO | WO-2014/162121 A1 | 10/2014 |
| WO | WO-2014/162122 A1 | 10/2014 |
| WO | WO-2014/162126 A1 | 10/2014 |
| WO | WO-2015/075483 A1 | 5/2015 |
| WO | WO-2015/092423 A1 | 6/2015 |
| WO | WO-2015/121444 A1 | 8/2015 |
| WO | WO-2015/121660 A1 | 8/2015 |
| WO | WO-2016/051186 A1 | 4/2016 |
| WO | WO-2016/051187 A1 | 4/2016 |
| WO | WO-2016/051188 A1 | 4/2016 |

OTHER PUBLICATIONS

Akula et al.,"Raf promotes human herpesvirus-8 (HHV-8/KSHV) infection," Oncogene. 23(30):5227-5241 (2004).

Alon et al., "Vascular endothelial growth factor acts as a survival factor for newly formed retinal vessels and has implications for retinopathy of prematurity," Nat Med. 1(10):1024-1028 (1995).

Ananthanarayanan et al., "Reaction of azides in presence of aluminium chloride," Indian J Chem. 27B:156-7 (1988).

Anastasaki et al.,"Continual low-level MEK inhibition ameliorates cardio-facio-cutaneous phenotypes in zebrafish," Dis Model Mech. 5(4):546-552 (2012).

Angerer et al., "Demonstration of tissue-specific gene expression by in situ hybridization," Methods Enzymol. 152:649-61 (1987).

Antony et al.,"C-RAF Mutations confer resistance to RAF inhibitors," Cancer Res. 73(15):4840-4851 (2013).

Arcaini et al., "The BRAF V600E mutation in hairy cell leukemia and other mature B-cell neoplasms," Blood. 119(1):188-191 (2012) (5 pages).

Asrih et al., "Role of mitogen-activated protein kinase pathways in multifactorial adverse cardiac remodeling associated with metabolic syndrome," Mediators Inflamm. 2013:367245 (2013) (12 pages).

Auvray et al., "Preparation and nucleophilic substitution of (E)-1-bromo-2-phenylsulfonyl-2-alkenes and 3-acetoxy-2-phenylsulfonyl-1-alkenes," Tetrahedron. 44(19):6095-106 (1988).

Avenoza et al., "New efficient synthesis of 4-amino-3-arylphenols," Synthesis. 671-674 (1995).

Badalian-Very et al., "Recent advances in the understanding of Langerhans cell histiocytosis," Br J Haematol. 156(2): 163-172 (2012).

Ballesteros et al., "Study of the catalytic properties of tris (3,6-dioxaheptyl) amine (tda-1) in heteroaromatic nucleophilic substitution of chloropyridines and their n-oxides," Tetrahedron. 43(11):2557-64 (1987).

Bart et al., "Development of novel, highly potent inhibitors of V-RAF murine sarcoma viral oncogene homologue B1 (BRAF): increasing cellular potency through optimization of a distal heteroaromatic group," J Med Chem. 53:2741-56 (2010).

Bates et al., "A new synthesis of pyrazinol[2,3-c]isoquinolines," Aust J Chem. 43(1): 179-184 (1990).

Bekerman et al., "Comparative kinetic studies on the synthesis of quinoxalinone derivatives and pyrido[2,3-b]pyrazinone derivatives by the hinsberg reaction," J Heterocyclic Chem. 29:129-33 (1992).

Belgore et al., "Localisation of members of the vascular endothelial growth factor (VEGF) family and their receptors in human atherosclerotic arteries," J Clin Pathol. 57(3): 266-272 (2004).

(56) References Cited

OTHER PUBLICATIONS

Benn et al., "Hepatitis B virus HBx protein activates Ras-GTP complex formation and establishes a Ras, Raf, MAP kinase signaling cascade," Proc Natl Acad Sci USA. 91(22): 10350-10354 (1994).
Berge et al., "Pharmaceutical salts," J Pharm Sci. 66(1):1-19 (1977).
Bergman et al., "Synthesis of pyridopyrazino[2,3-b]indoles and 10H-indolo[3,2-g]pteridins," Recl Tray Chim Pays-Bas. 115(1): 31-36 (1996).
Berry et al., "TNF-alpha in asthma," Curr Opin Pharmacol. 7(3): 279-282 (2007).
Bhatt et al., "Preparation of $N^1$-2-phenyl-4-quinolinoyl-$N^3$-aryl thioureas," J Instit Chem (India). 52:113-4 (1980).
Bianchi et al., "Compounds with antiulcer and antisecretory activity," Eur J Med Chem. 16(4):321-6 (1981).
Borthakur et al., "New direct synthesis of thioamides from carboxylic acids," Tetrahedron Letters. 36(37):6745-6 (1995).
Bos, "Ras oncogenes in human cancer: a review," Cancer Res. 49(17):4682-9 (1989).
Broekhof et al., "Novel applications of alpha-aminosubstituted diphenylphosphine oxides. The conversion of aldehydes into alpha-aminomethylketones," Tetrahedron Lett. 22(29):2799-802 (1981).
Brooks et al., "Integrin alpha v beta 3 antagonists promote tumor regression by inducing apoptosis of angiogenic blood vessels," Cell. 79(7): 1157-64 (1994).
Brose et al., "BRAF and RAS mutations in human lung cancer and melanoma," Cancer Res. 62(23):6997-7000 (2002).
Bruckner et al.,"Tyrosine phosphorylation of transmembrane ligands for Eph receptors," Science. 275(5306):1640-3 (1997).
Bruder et al., "Serum-, TPA-, and Ras-induced expression from Ap-1/Ets-driven promoters requires Raf-1 kinase," Genes Dev. 6(4):545-56 (1992).
Byeon et al., "The role of Src kinase in macrophage-mediated inflammatory responses," Mediators Inflamm. 2012:512926 (2012) (19 pages).
Calhoun et al., "BRAF and FBXW7 (CDC4, FBW7, AGO, SEL10) mutations in distinct subsets of pancreatic cancer: potential therapeutic targets," Am J Pathol. 163(4): 1255-1260 (2003).
Cantrell, "GTPases and T cell activation," Immunol Rev.192:122-30 (2003).
Chan et al., "Regulation of antigen receptor signal transduction by protein tyrosine kinases," Curr Opin Immunol. 8(3):394-401 (1995).
Chapman et al., "Improved survival with vemurafenib in melanoma with BRAF V600E mutation," N Engl J Med. 364(26): 2507-2516 (2011).
Chapman et al., "Initial genome sequencing and analysis of multiple myeloma," Nature 471(7339):467-72 (2011).
Ciampi et al., "Oncogenic AKAP9-BRAF fusion is a novel mechanism of MAPK pathway activation in thyroid cancer," J Clin Invest. 115(1): 94-101 (2005).
Clare et al., "Protease inhibitors: synthesis of a series of bacterial collagenase inhibitors of the sulfonyl amino acyl hydroxamate type," J Med Chem. 44(13):2253-8 (2001).
Clark-Lewis et al., "Quinoxaline derivatives. Part IV. Dihydro-oxo-1 : 4 : 5-triazanaphthalenecarboxyureides and related spiroHydantoins," J Chem Soc. 430-439 (1957).
Cohen et al., "Lack of BRAF mutation in primary uveal melanoma," Invest Ophthalmol Vis Sci. 44(7):2876-8 (2003).
Colville-Nash et al., "Angiogenesis and rheumatoid arthritis: pathogenic and therapeutic implications," Ann Rheum Dis. 51(7):919-25 (1992).
Comins et al., "Grignard addition to 1-acyl salts of chiral 4-alkoxypyridines. A new enantioselective preparation of 2-alkyl-2,3-dihydro-4-pyridones," Tetrahedron Lett. 35(40):7343-6 (1994).
Cooper, "Membrane-associated tyrosine kinases as molecular switches," Semin Cell Biol. 5(6):377-87 (1994).
Corcoran et al., "BRAF gene amplification can promote acquired resistance to MEK inhibitors in cancer cells harboring the BRAF V600E mutation," Sci Signal. 3(149):ra84 (2010) (10 pages).
Correia, "Reaction of phenylglyoxal with aniline under acidic conditions," J Org Chem 43(17):3394-6 (1978).
Coulthard et al., "p38(MAPK): stress responses from molecular mechanisms to therapeutics," Trends Mol Med. 15(8): 369-379 (2009).
Courtneidge et al., "The Src family of protein tyrosine kinases: regulation and functions," Dev Suppl. 57-64 (1993).
Cowely et al., "Activation of MAP kinase kinase is necessary and sufficient for PC12 differentiation and for transformation of NIH 3T3 cells," Cell. 77(6):841-52 (1994).
Cuadrado et al., "Mechanisms and functions of p38 MAPK signalling," Biochem J. 429(3): 403-417 (2010).
Cushman et al., "19F NMR studies on the mechanism of riboflavin synthase. Synthesis of 6-(Trifluoromethyl)-7-oxo-8-(D-ribityl-)lumazine and 6-(Trifluoromethyl)-7-methyl-8-(D-ribityl-)lumazine," J Org Chem. 57(21): 5630-5643 (1992).
Davies et al., "Mutations of the BRAF gene in human cancer," Nature. 417(6892):949-54 (2002).
Davis et al., "Isolation of angiopoietin-1, a ligand for the TIE2 receptor, by secretion-trap expression cloning," Cell. 87(7):1161-9 (1996).
Davis et al., "Raf and mitogen-activated protein kinase regulate stellate cell collagen gene expression," J Biol Chem. 271(19): 11039-11042 (1996) (5 pages).
Denekamp, "Review article: angiogenesis, neovascular proliferation and vascular pathophysiology as targets for cancer therapy," Br J Radiol. 66(783):181-96 (1993).
Dettner et al., "Chemical defense of giant springtail Tetrodontophora bielanensis (Waga) (Insecta: Collembola)," J Chem Ecol. 22(5): 1051-1074 (1996).
Dhomen et al., "Oncogenic Braf induces melanocyte senescence and melanoma in mice," Cancer Cell. 15(4): 294-303 (2009).
Dickson et al., "Raf functions downstream of Ras1 in the Sevenless signal transduction pathway," Nature. 360(6404):600-3 (1992).
Downward, "Targeting RAS signalling pathways in cancer therapy," Nat Rev Cancer. 3(1):11-22 (2003).
Dubey et al., "Structure and reactions of monoanils obtained from 2,3-pyridinediamines," Indian J Chem. 40B(5): 361-367 (2001).
DuBois, "Amination of aryl sulfamate esters. A convenient general synthesis of aliphatic sulfamides," J Org Chem. 45:5373-5 (1980).
Ellis et al., "VEGF-targeted therapy: mechanisms of anti-tumour activity," Nat Rev Cancer. 8(8): 579-591 (2008).
Falchook et al., "RAF inhibitor dabrafenib (GSK2118436) is active in melanoma brain metastases, multiple BRAF genotypes and diverse cancers" NIH Public Access Author Manuscript 20 pages Jul. 24, 2014, published in final edited form as "Dabrafenib in patients with melanoma, untreated brain metastases, and other solid tumours: a phase 1 dose-escalation trial," Lancet. 379(9829): 1893-1901 (2012).
Fernandez-Medarde et al., "Ras in cancer and developmental diseases," Genes Cancer. 2(3): 344-358 (2011).
Fidler et al., "The implications of angiogenesis for the biology and therapy of cancer metastasis," Cell. 79(2):185-8 (1994).
Flaherty et al., "Inhibition of mutated, activated BRAF in metastatic melanoma," N Engl J Med. 363(9): 809-819 (2010).
Folkman et al., "Angiogenesis," J Biol Chem. 267(16):10931-4 (1992).
Folkman, "Angiogenesis and angiogenesis inhibition: An overview," EXS. 79:1-8 (1997).
Folkman, "Angiogenesis in cancer, vascular, rheumatoid and other disease," Nat Med. 1(1):27-31 (1995).
Folkman, "The role of angiogenesis in tumor growth," Semin Cancer Biol. 3(2):65-71 (1992).
Fourrey et al., "Preparation of stable 1,4-dihydropyrazines," J Chem Soc., Perkins Transactions 1: Org. and Bio. Chem. 8:1841-3 (1987).
Friedlander et al., "Definition of two angiogenic pathways by distinct alpha v integrins," Science. 270(5241):1500-2 (1995).
Fujita et al., "ERK and p38 mediate high-glucose-induced hypertrophy and TGF-beta expression in renal tubular cells," Am J Physiol Renal Physiol. 286(1): F120-6 (2004).
Fukuda et al., "Epstein-Barr virus latent membrane protein 2A mediates transformation through constitutive activation of the Ras/PI3-K/Akt Pathway," J Virol. 81(17): 9299-9306 (2007).

(56) References Cited

OTHER PUBLICATIONS

Gale et al., "Growth factors acting via endothelial cell-specific receptor tyrosine kinases: VEGFs, angiopoietins, and ephrins in vascular development," Genes Dev. 13(9):1055-1066 (1999).
Galons, "Cyclisation indolique selon Bischler en presence d'acides de Lewis," J Heterocyclic Chemistry. 18:561-63 (1981).
Garnett et al., "Guilty as charged: B-RAF is a human oncogene," Cancer Cell. 6(4):313-9 (2004).
Gaudi et al., "Molecular bases of cutaneous and uveal melanomas," Patholog Res Int. 2011:159421 (2011) (8 pages).
Genot et al.,"Ras regulation and function in lymphocytes," Curr Opin Immunol. 12(3):289-94 (2000) (6 pages).
Geppert et al., "Lipopolysaccharide signals activation of tumor necrosis factor biosynthesis through the ras/raf-1/MEK/MAPK pathway," Mol Med. 1(1): 93-103 (1994).
Giannotti et al., "New dibenzothiadiazepine derivatives with antidepressant activities," J Med Chem 34(4):1356-62 (1991).
Giardina et al., "Replacement of the quinoline system in 2-phenyl-4-quinolinecarboxamide NK-3 receptor antagonists," Farmaco. 54(6):364-74 (1999).
Girotti et al., "Inhibiting EGF receptor or SRC family kinase signaling overcomes BRAF inhibitor resistance in melanoma," Cancer Discov. 3(2): 158-167 (2013).
Glinka, "Synthesis and structure of new hetercyclic systems containing the sulfamide group," Pol J Chem. 65:2053-5 (1991).
Golub et al., "Molecular classification of cancer: class discovery and class prediction by gene expression monitoring," Science. 286(5439):531-7 (1999).
Gorden et al., "Analysis of BRAF and N-RAS mutations in metastatic melanoma tissues," Cancer Res. 63(14):3955-7 (2003).
Graf et al., "Mitogen-activated protein kinase activation is involved in platelet-derived growth factor-directed migration by vascular smooth muscle cells," Hypertension. 29(1 Pt. 2): 334-339 (1997).
Gray-Schopfer et al., "Melanoma biology and new targeted therapy," Nature. 445(7130):851-7 (2007).
Greger et al., "Combinations of BRAF, MEK, and PI3K/mTOR inhibitors overcome acquired resistance to the BRAF inhibitor GSK2118436 dabrafenib, mediated by NRAS or MEK mutations," Mol Cancer Ther. 11(4): 909-920 (2012).
Grosios et al., "Angiogenesis inhibition by the novel VEGF receptor tyrosine kinase inhibitor, PTK787/ZK222584, causes significant anti-arthritic effects in models of rheumatoid arthritis," Inflamm Res. 53(4): 133-142 (2004).
Guarna et al., "Synthesis of a new enantiopure bicyclic gamma/delta-amino acid (BTKa) derived from tartaric acid and alpha-amino acetophenone," Tetrahedron. 58(49):9865-70 (2002).
Haase et al., "A role for mitogen-activated protein kinase activation by integrins in the pathogenesis of psoriasis," J Clin Invest. 108(4): 527-536 (2001).
Haesslein et al., "Recent advances in cyclin-dependent kinase inhibition. Purine-based derivatives as anti-cancer agents. Roles and perspectives for the future," Curr Top Med Chem. 2(9):1037-50 (2002).
Hammond et al., "Structure-activity relationships in a series of NPY Y5 antagonists: 3-amido-9-ethylcarbazoles, core-modified analogues and amide isosteres," Bioorg Med Chem Lett. 13(12):1989-92 (2003).
Haroche et al., "High prevalence of BRAF V600E mutations in Erdheim-Chester disease but not in other non-Langerhans cell histiocytoses," Blood. 120(3): 2700-2703 (2012) (5 pages).
Heidorn et al., "Kinase-dead BRAF and oncogenic RAS cooperate to drive tumor progression through CRAF," Cell. 140(2): 209-221 (2010).
Helbling et al., "The receptor tyrosine kinase EphB4 and ephrin-B ligands restrict angiogenic growth of embryonic veins in Xenopus laevis," Development. 127(2):269-78 (2000).
Hirayama et al., "Design, synthesis and biological activity of YM-60828 derivatives: potent and orally-bioavailable factor Xa inhibitors based on naphthoanilide and naphthalensulfonanilide templates," Bioorg Med Chem. 10(8):2597-610 (2002).
Holland et al., "Bidirectional signalling through the EPH-family receptor Nuk and its transmembrane ligands," Nature. 383(6602):722-5 (1996).
Hu et al., "Mutation that blocks ATP binding creates a pseudokinase stabilizing the scaffolding function of kinase suppressor of Ras, CRAF and BRAF," Proc Natl Acad Sci USA. 108(15): 6067-6072 (2011) (9 pages).
Hwang et al., "Over-expression of c-raf-1 proto-oncogene in liver cirrhosis and hepatocellular carcinoma," Hepatol Res. 29(2): 113-121 (2004).
Ingber et al., "Synthetic analogues of fumagillin that inhibit angiogenesis and suppress tumour growth," Nature. 348(6301):555-7 (1990).
Inoue et al., "Vascular endothelial growth factor (VEGF) expression in human coronary atherosclerotic lesions: possible pathophysiological significance of VEGF in progression of atherosclerosis," Circulation. 98(20): 2108-2116 (1998).
International Preliminary Report on Patentability for International Application No. PCT/GB2005/004081, issued Apr. 24, 2007 (8 pages).
International Preliminary Report on Patentability for International Application No. PCT/GB2007/001534, issued Oct. 28, 2008 (10 pages).
International Preliminary Report on Patentability for International Application No. PCT/GB2008/004208, issued Jun. 22, 2010 (6 pages).
International Preliminary Report on Patentability for International Application No. PCT/GB2009/001077, issued Oct. 26, 2010 (6 pages).
International Preliminary Report on Patentability for International Application No. PCT/GB2011/000106, issued Aug. 7, 2012 (7 pages).
International Preliminary Report on Patentability for International Application No. PCT/GB2014/053489, issued May 31, 2016 (6 pages).
International Preliminary Report on Patentability for International Application No. PCT/GB2014/053490, issued May 31, 2016 (7 pages).
International Search Report and Written Opinion for International Application No. PCT/GB2005/004081, mailed Feb. 2, 2006 (12 pages).
International Search Report and Written Opinion for International Application No. PCT/GB2008/004208, mailed Mar. 5, 2009 (7 pages).
International Search Report and Written Opinion for International Application No. PCT/GB2009/001077, mailed Sep. 21, 2009 (8 pages).
International Search Report and Written Opinion for International Application No. PCT/GB2011/000106, mailed Mar. 18, 2011 (10 pages).
International Search Report and Written Opinion for International Application No. PCT/GB2014/053489, mailed Jan. 15, 2015 (11 pages).
International Search Report and Written Opinion for International Application No. PCT/GB2014/053490, mailed Jan. 26, 2015 (10 pages).
International Search Report for International Application No. PCT/GB2007/001534, mailed Sep. 6, 2007 (4 pages).
Ishii et al., "First synthesis and reactivities of isolable dithiiranes and their 1-oxides," Bulletin of the Chemical Society of Japan. 70:509-23 (1997).
Itaya et al., "Syntheses of the marine ascidian purine aplidiamine and its 9-beta-d-ribofuranoside," Tetrahedron Lett. 39:4695-6 (1998).
Jaffee et al., "Inhibition of MAP kinase kinase (MEK) results in an anti-inflammatory response in vivo," Biochem Biophys Res Commun. 268(2): 647-651 (2000).
Janvier et al., "Ammonium chloride-promoted four-component synthesis of pyrrolo[3,4-b]pyridin-5-one," J Am Chem Soc. 124(11):2560-7 (2002).
Jessen et al., "MEK inhibition exhibits efficacy in human and mouse neurofibromatosis tumors," J Clin Invest 123(1): 340-347 (2013).

(56) References Cited

OTHER PUBLICATIONS

Ji et al., "ERK MAP kinase activation in superficial spinal cord neurons induces prodynorphin and NK-1 upregulation and contributes to persistent inflammatory pain hypersensitivity," J Neurosci. 22(2): 478-85 (2002).
Jo et al., "MEK inhibitor, U0126, attenuates cisplatin-induced renal injury by decreasing inflammation and apoptosis," Kidney Int. 67(2): 458-466 (2005).
Johnson et al., "Preparation and reactions of sulfonimidoyl chlorides," J Org Chem. 44(13):2055-61 (1979).
Johnson et al., "The role of MKK1/2 kinase activity in human cytomegalovirus infection," J Gen Virol. 82(Pt 3): 493-497 (2001).
Jursic, "Synthetic application of micellar catalysis. williamson's synthesis of ethers," Tetrahedron. 44(21):6677-80 (1988).
Kahlon et al., "Angiogenesis in atherosclerosis," Can J Cardiol. 8(1):60-4 (1992).
Kam et al.,"TNF-alpha antagonists for the treatment of Crohn's disease," Expert Opin Pharmacother. 1(4): 615-622 (2000).
Karim et al.,"Impaired inflammatory pain and thermal hyperalgesia in mice expressing neuron-specific dominant negative mitogen activated protein kinase kinase (MEK)," Mol Pain. 2: 2 (2006) (10 pages).
Keffer et al., "Transgenic mice expressing human tumour necrosis factor: a predictive genetic model of arthritis," EMBO J. 10(13): 4025-4031 (1991).
Kolch et al., "Raf-1 protein kinase is required for growth of induced NIH/3T3 cells," Nature. 349(6308):426-8 (1991).
Kotoula et al., "Mutational analysis of the BRAF, RAS and EGFR genes in human adrenocortical carcinomas," Endocr Relat Cancer. 16(2): 565-572 (2009).
Lala et al., "Role of nitric oxide in tumor progression: lessons from experimental tumors," Cancer Metastasis Rev. 17(1):91-106 (1998).
Leese et al., "Polyazanaphthalenes. Part I. Some derivatives of 1:4:5-triazanaphthalene and quinoxaline," J Chem Soc. 303-309 (1955).
Lemonnier et al., "Role of N-cadherin and protein kinase C in osteoblast gene activation induced by the S252W fibroblast growth factor receptor 2 mutation in Apert craniosynostosis," J Bone Miner Res. 16(5):832-45 (2001).
Li et al., "Activation of NF-kappaB via a Src-dependent Ras-MAPK-pp90rsk pathway is required for Pseudomonas aeruginosa-induced mucin overproduction in epithelial cells," Proc Natl Acad Sci USA. 95(10): 5718-5723 (1998).
Lin et al., "VEGF and its receptor-2 involved in neuropathic pain transmission mediated by P2X2(/)3 receptor of primary sensory neurons," Brain Res Bull. 83(5):284-291 (2010).
Lindauer et al., "Dasatinib," Recent Results Cancer Res. 184: 83-102 (2010).
Link et al., "Phosphodiesterase 4 inhibition but not beta-adrenergic stimulation suppresses tumor necrosis factor-alpha release in peripheral blood mononuclear cells in septic shock," Crit Care. 12(6):R159 (2008) (9 pages).
Liu et al., "Effects of overexpression of ephrin-B2 on tumour growth in human colorectal cancer," Br J Cancer. 90(8):1620-6 (2004).
Long et al., "Prognostic and clinicopathologic associations of oncogenic BRAF in metastatic melanoma," J Clin Oncol. 29(10): 1239-1246 (2011).
Lorenz et al., "Cardiac hypertrophy: targeting Raf/MEK/ERK1/2-signaling," Int J Biochem Cell Biol. 41(12): 2351-2355 (2009).
Lowenberg et al.,"Specific inhibition of c-Raf activity by semapimod induces clinical remission in severe Crohn's disease," J Immunol. 175(4): 2293-2300 (2005).
Lozinskii et al., "Alkylthio derivatives of the aminoketene S,N-Acetals of heterocyclic beta-dicarbonyl compounds: one stage synthesis and properties," Chemistry of Heterocyclic Compounds. 38(9):1077-80 (2002).
Luo et al., "Coxsackievirus B3 replication is reduced by inhibition of the extracellular signal-regulated kinase (ERK) signaling pathway," J Virol. 76(7): 3365-3373 (2002).

Ma et al., "The ERK/MAPK pathway, as a target for the treatment of neuropathic pain," Expert Opin Ther Targets. 9(4):699-713 (2005).
Maddahi et al.,"Cerebral ischemia induces microvascular pro-inflammatory cytokine expression via the MEK/ERK pathway," J Neuroinflammation. 7:14 (2010) (13 pages).
Mammas et al., "Involvement of the ras genes in female genital tract cancer," Int J Oncol. 26(5):1241-1255 (2005).
Mansour et al., "Transformation of mammalian cells by constitutively active MAP kinase kinase," Science. 265(5174):966-70 (1994).
Marais et al., "Differential regulation of Raf-1, A-Raf, and B-Raf by oncogenic ras and tyrosine kinases," J Biol Chem. 272(7):4378-83 (1997).
Martich et al., "Detection of interleukin 8 and tumor necrosis factor in normal humans after intravenous endotoxin: the effect of antiinflammatory agents," J Exp Med. 173(4):1021-1024 (1991).
Martin et al., "Update on lymphocyte specific kinase inhibitors: a patent survey," Expert Opin Ther Pat. 20(11): 1573-1593 (2010).
Mashelkar et al., "Synthesis of some novel 4-substituted coumarins having potential biological activity (Part II)," Indian J Chem. 45B(4): 967-971 (2006).
Mataloni et al., "Synthesis of secondary amines by reduction of alpha-amidoalkylphenyl sulfones with sodium acetoxyborohydride," Synlett. 8:1129-32 (2003).
McCann et al.,"Apremilast, a novel PDE4 inhibitor, inhibits spontaneous production of tumour necrosis factor-alpha from human rheumatoid synovial cells and ameliorates experimental arthritis," Arthritis Res Ther. 12(3): R107 (2010) (11 pages).
McKay et al., "Complexity in KSR function revealed by Raf inhibitor and KSR structure studies," Small GTPases. 2(5):276-281 (2011) (7 pages).
McKillop et al., "Applications of ethyl carboethoxyformimidate to heterocyclic synthesis: preparation of condensed pyrazinones and 1,4-oxazinones," Synthesis. 3:301-304 (1997).
McMahon, "VEGF receptor signalling in tumor angiogenesis," Oncologist. 5(suppl 1):3-10 (2000).
Mei et al., "Distribution, levels and phosphorylation of Raf-1 in Alzheimer's disease," J Neurochem. 99(5): 1377-1388 (2006).
Menard et al., "Novel potent BRAF inhibitors: toward 1 nM compounds through optimization of the central phenyl ring," J Med Chem. 52(13): 3881-3891 (2009).
Mercer et al., "Emerging role of MAP kinase pathways as therapeutic targets in COPD," Int J Chron Obstruct Pulmon Dis. 1(2):137-150 (2006).
Messinger et al., "Synthesis of alpha-amino- and alpha-amidosulfones. 5. Sulfones as chemical transport forms of substances with germicidae effect," Arch Pharm (Weinheim). 307(8):653-5 (1974). (In German with partial English language translation).
Metzner et al., "Fibroblast growth factor receptors as therapeutic targets in human melanoma: synergism with BRAF inhibition," J Invest Dermatol. 131(10): 2087-2095 (2011).
Meyers et al., "FGFR2 exon IIIa and IIIc mutations in Crouzon, Jackson-Weiss, and Pfeiffer syndromes: evidence for missense changes, insertions, and a deletion due to alternative RNA splicing," Am J Hum Genet. 58(3):491-8 (1996).
Milella et al., "Therapeutic targeting of the MEK/MAPK signal transduction module in acute myeloid leukemia," J Clin Invest. 108(6): 851-859 (2001).
Mineo et al., "Prognostic impact of VEGF, CD31, CD34, and CD105 expression and tumour vessel invasion after radical surgery for IB-IIA non-small cell lung cancer," J Clin Pathol. 57(6):591-7 (2004).
Miura et al., "Simvastatin suppresses coronary artery endothelial tube formation by disrupting Ras/Raf/ERK signaling," Atherosclerosis. 175(2): 235-243 (2004).
Mohanta et al., "1-(methyldithiocarbony)imidazole: a useful thiocarbonyl transfer reagent for synthesis of substituted thioureas," Tetrahedron. 56(4):629-37 (2000).
Montagut et al., "Elevated CRAF as a potential mechanism of acquired resistance to BRAF inhibition in melanoma," Cancer Res. 68(12): 4853-4861 (2008) (16 pages).

(56) References Cited

OTHER PUBLICATIONS

Moore et al., "ROMP-generated oligomeric sulfonyl chlorides as versatile soluble scavenging agents," Org Lett. 5(2):105-7 (2003).
Mukherjee et al., "Raf-1 expression may influence progression to androgen insensitive prostate cancer," Prostate. 64(1):101-107 (2005).
Mukhopadhyay et al., "Role of TNFalpha in pulmonary pathophysiology," Respir Res. 7:125 (2006) (9 pages).
Mustonen et al., "Endothelial receptor tyrosine kinases involved in angiogenesis," J Cell Biol. 129(4):895-8 (1995).
Nakamoto et al., "Diverse roles for the Eph family of receptor tyrosine kinases in carcinogenesis," Miscrosc Res Tech. 59(1):58-67 (2002).
Nakamura et al., "Novel strategies for the treatment of inflammatory bowel disease: Selective inhibition of cytokines and adhesion molecules," World J Gastroenterol. 12(29): 4628-4635 (2006).
Nazarian et al., "Melanomas acquire resistance to B-RAF(V600E) inhibition by RTK or N-RAS upregulation," Nature. 468(7326): 973-977 (2010) (7 pages).
O'Reilly et al., "Angiostatin: a novel angiogenesis inhibitor that mediates the suppression of metastases by a Lewis lung carcinoma," Cell. 79(2):315-28 (1994).
Oeztuerk-Winder et al., "The many faces of p38 mitogen-activated protein kinase in progenitor/stem cell differentiation," Biochem J. 445(1): 1-10 (2012).
Orre et al., "VEGF, VEGFR-1, VEGFR-2, microvessel density and endothelial cell proliferation in tumours of the ovary," Int J Cancer. 84(2):101-8 (1999).
Ozawa et al., "Growth factors and their receptors in pancreatic cancer," Teratog Carcinog Mutagen. 21(1):27-44 (2001).
Pabst et al., "Analysis of K-ras mutations in pancreatic tissue after fine needle aspirates," Anticancer Res. 19(4A):2481-3 (1999).
Palanisamy et al., "Rearrangements of the RAF kinase pathway in prostate cancer, gastric cancer and melanoma," Nat. Med. 16(7): 793-798 (2010) (7 pages).
Parlow et al., "Synthesis and crystal structures of substituted benzenes and benzoquinones as tissue factor VIIa inhibitors," J Med Chem. 46(20):4297-4312 (2003).
Partanen et al., "A novel endothelial cell surface receptor tyrosine kinase with extracellular epidermal growth factor homology domains," Mol Cell Biol. 12(4):1698-707 (1992).
Partanen et al., "Functions of Tie1 and Tie2 receptor tyrosine kinases in vascular development," Curr Top Microbiol Immunol. 237:159-72 (1999).
Patani et al., "Bioisosterism: a rational approach to drug design," Chem Rev. 96(8):3147-76 (1996).
Paulson et al., "Receptor tyrosine kinases and the regulation of hematopoiesis," Semin Immunol. 7(4):267-77 (1995).
Payne et al., "Human papillomavirus type 6b virus-like particles are able to activate the Ras-MAP kinase pathway and induce cell proliferation," J Virol. 75(9): 4150-4157 (2001).
Peacock et al., "A novel angiogenesis inhibitor suppresses rat adjuvant arthritis," Cell Immunol. 160(2):178-84 (1995).
Peacock et al., "Angiogenesis inhibition suppresses collagen arthritis," J Exp Med. 175(4):1135-8 (1992).
Pelletier et al., "In vivo selective inhibition of mitogen-activated protein kinase kinase ½ in rabbit experimental osteoarthritis is associated with a reduction in the development of structural changes," Arthritis Rheum. 48(6): 1582-1593 (2003).
Peters, "Vascular endothelial growth factor and the angiopoietins working together to build a better blood vessel," Circ Res. 83(3):342-3 (1998).
Petrovan et al., "DNA vaccination against VEGF receptor 2 reduces atherosclerosis in LDL receptor-deficient mice," Arterioscler Thromb Vasc Biol. 27(5): 1095-1100 (2007) (11 pages).
Pinedo et al., "Translational research: the role of VEGF in tumor angiogenesis," The Oncologist. 5:1-2 (2000).
Planz et al., "MEK-specific inhibitor U0126 blocks spread of Borna disease virus in cultured cells," J Virol. 75(10): 4871-4877 (2001).
Pleschka et al., "Influenza virus propagation is impaired by inhibition of the Raf/MEK/ERK signalling cascade," Nat Cell Biol. 3(3): 301-305 (2001) (7 pages).
Plomp et al., "Pfeiffer syndrome type 2: further delineation and review of the literature," Am J Med Genet. 75(3):245-51 (1998).
Poulikakos et al., "RAF inhibitor resistance is mediated by dimerization of aberrantly spliced BRAF(V600E)," Nature. 480(7377): 387-390 (2011) (5 pages).
Poulikakos et al., "RAF inhibitors transactivate RAF dimers and ERK signalling in cells with wild-type BRAF," Nature. 464(7287): 427-430 (2010) (5 pages).
Powers et al., "Fibroblast growth factors, their receptors and signalling," Endocr Relat Cancer. 7(3):165-97 (2000).
Prakash et al., " A convenient synthesis of alpha-anilinoacetophenones using hypervalent iodine," Indian Journal of Chemistry, Section B: Organic Chemistry Including Medicinal Chemistry. 31:349-50 (1992).
Prix et al., "Diagnostic biochip array for fast and sensitive detection of K-ras mutations in stool," Clin Chem. 48(3):428-35 (2002).
Rajagopalan et al., "Tumorgenesis: RAF/RAS oncogenes and mismatch-repairs status," Nature. 418(6901):934 (2002).
Ramadas et al., "LAC sulfur assisted synthesis of symmetrical thioureas," Synth Comm. 27(13):2255-60 (1997).
Reck et al., "Novel N-linked aminopiperidine inhibitors of bacterial topoisomerase type II: broad-spectrum antibacterial agents with reduced hERG activity," J Med Chem. 54(22): 7834-7847 (2011).
Damodar Reddy et al., "Role of MAP kinase pathways in primitive neuroectodermal tumors," Anticancer Res. 21(4A): 2733-8 (2001).
Remli et al., "Reaction of o-arylenediamines with ethyl 3-fluoro 2-ketoesters synthesis of quinoxaline derivatives," J Fluorine Chem. 44: 15-23 (1989).
Riva et al., "Differential c-myc, c-jun, c-raf and p53 expression in squamous cell carcinoma of the head and neck: implication in drug and radioresistance," Eur J Cancer B Oral Oncol. 31 B(6): 384-391 (1995).
Rotsos et al., "Cystoid macular edema," Clin Ophthalmol. 2(4): 919-930 (2008).
Rubinstein et al., "Incidence of the V600K mutation among melanoma patients with BRAF mutations, and potential therapeutic response to the specific BRAF inhibitor PLX4032," J Transl Med. 8: 67 (2010) (3 pages).
Rudy et al., "Zweikernige Alloxan-Abkömmlinge von 2.3-Diaminopyridinen," Chemische Berichte. 71:1323-1332 (1938) (Abstract Included) (11 pages).
Salama et al., "BRAF in Melanoma: Current strategies and future directions," Clin Cancer Res. 19(16): 4326-4334 (2013).
Sarkis et al., "Synthesis and spectroscopic properties of some new N,N'-disubstituted thioureas of potential biological interest," J Heterocyclic Chemistry. 22:137-40 (1985).
Schindler et al., "Analysis of BRAF V600E mutation in 1,320 nervous system tumors reveals high mutation frequencies in pleomorphic xanthoastrocytoma, ganglioglioma and extra-cerebellar pilocytic astrocytoma," Acta Neuropathol. 121(3): 397-405 (2011).
Schreck et al., "Raf kinases: Oncogenesis and drug discovery," Int J Cancer. 119(10): 2261-2271 (2006).
Search Report for British Application No. GB 0423554.5, dated Feb. 23, 2005 (1 page).
Search Report for British Application No. GB 0608268.9, dated Aug. 9, 2006 (1 page).
Search Report for British Application No. GB 0807609.3, dated Aug. 21, 2008 (2 pages).
Search Report for United Kingdom Application No. GB 1320729.5, dated May 20, 2014 (2 pages).
Search Report for United Kingdom Application No. GB 1320732.9, dated May 19, 2014 (2 pages).
Seki et al., "Reaction products of dialkyl acetylenedicarboxylates with 2,3-diaminopyridine," J Heterocyclic Chem. 32(3): 1071-1073 (1995).
Shakhov et al., "Kappa B-type enhancers are involved in lipopolysaccharide-mediated transcriptional activation of the tumor necrosis factor alpha gene in primary macrophages," J Exp Med. 171(1): 35-47 (1990).

(56) References Cited

OTHER PUBLICATIONS

Shapira et al., "Protection against endotoxic shock and lipopolysaccharide-induced local inflammation by tetracycline: correlation with inhibition of cytokine secretion," Infect Immun. 64(3): 825-828 (1996).
Shaw et al.,"The preparation of 2,6-diaminopyrazine, 2,6-diazidopyrazine and some of their derivatives," J Heterocycl Chem. 17(1): 11-6 (1980).
Sherman et al., "Synthesis of unsymmetrical and regio-defined 2,3,6-quinoxaline and 2,3,7-pyridopyrazine derivatives," Tetrahedron Lett. 48(51):8943-8946 (2007).
Shi et al., "Melanoma whole-exome sequencing identifies (V600E)B-RAF amplification-mediated acquired B-RAF inhibitor resistance," Nat Commun. 3: 724 (2012) (8 pages).
Shibuya, "Vascular endothelial growth factor and its receptor system: physiological functions in angiogenesis and pathological roles in various diseases," J Biochem. 153(1):13-19 (2013).
Shiina et al., "A new method for the synthesis of carboxamides and peptides using 1,1'-carbonyldioxydi[2(1H)-pyridone] (CDOP) in the absence of basic promoters," Tetrahedron Letters. 44:1951-55 (2003).
Shin et al., "Expression of EphrinB2 identifies a stable genetic difference between arterial and venous vascular smooth muscle as well as endothelial cells, and marks subsets of microvessels at sites of adult neovascularization," Dev Biol. 230(2):139-50 (2001).
Sievert et al.,"Paradoxical activation and RAF inhibitor resistance of BRAF protein kinase fusions characterizing pediatric astrocytomas," Proc Natl Acad Sci USA. 110(15): 5957-5962 (2013) (9 pages).
Singer et al., "Mutations in BRAF and KRAS characterize the development of low-grade ovarian serous carcinoma," J Natl Cancer Inst. 95(6):484-6 (2003).
Smalley et al.,"CRAF inhibition induces apoptosis in melanoma cells with non-V600E BRAF mutations," Oncogene. 28(1): 85-94 (2009).
Smith et al.,"Vascular endothelial growth factor receptors VEGFR-2 and VEGFR-3 are localized primarily to the vasculature in human primary solid cancers," Clin Cancer Res. 16(14): 3548-3561 (2010).
Solit et al., "BRAF mutation predicts sensitivity to MEK inhibition," Nature. 439(7074):358-62 (2006).
Song et al., "Activation of ERK/CREB pathway in spinal cord contributes to chronic constrictive injury-induced neuropathic pain in rats," Acta Pharmacol Sin. 26(7): 789-98 (2005).
Sosman et al., "Survival in BRAF V600-mutant advanced melanoma treated with vemurafenib," N Engl J Med. 366(8):707-714 (2012).
Srinivas et al., "A highly convenient, efficient, and selective process for preparation of esters and amides from carboxylic acids using Fe(3+)-K-10-montmorillonite clay," J Org Chem. 68(3):1165-7 (2003).
Srivastava et al., "Synthesis and antithyroid activity of some benzimidazolyl and benzenesulphonyl thiocarbamides" Current Science. 50(7):305-7 (1981).
Straussman et al., "Tumour micro-environment elicits innate resistance to RAF inhibitors through HGF secretion," Nature. 487(7408): 500-504 (2012) (7 pages).
Suijkerbuijk et al., "Development of novel, highly potent inhibitors of V-RAF murine sarcoma viral oncogene homologue B1 (BRAF): increasing cellular potency through optimization of a distal heteroaromatic group," J Med Chem. 53(7):2741-56 (2010).
Sullivan et al., "BRAF in melanoma: pathogenesis, diagnosis, inhibition, and resistance," J Skin Cancer. 2011:423239 (2011) (8 pages).
Suri et al., "Requisite role of angiopoietin-1, a ligand for TIE2 receptor, during embryonic angiogenesis," Cell. 87(7):1171-80 (1996).
Tam et al., "Blockade of VEGFR2 and not VEGFR1 can limit diet-induced fat tissue expansion: role of local versus bone marrow-derived endothelial cells," PLoS One. 4(3):e4974 (2009) (6 pages).

Tang et al., "Coexpression of transcripts encoding EPHB receptor protein tyrosine kinases and their ephrin-B ligands in human small cell lung carcinoma," Clin Cancer Res. 5(2):455-60 (1999).
Tang et al., "High-level expression of EPHB6, EFNB2, and EFNB3 is associated with low tumor stage and high TrkA expression in human neuroblastomas," Clin Cancer Res. 5(6):1491-6 (1999).
Tanga et al., "Syntheses of two potential food mutagens," J Heterocycl Chem. 40(4):569-73 (2003).
Taraboletti et al., "Inhibition of angiogenesis and murine hemangioma growth by batimastat, a synthetic inhibitor of matrix metalloproteinases," J Natl Cancer Inst. 87(4):293-8 (1995).
Temple et al., "New anticancer agents: alterations of the carbamate group of ethyl (5-amino-1,2-dihydro-3-phenylpyrido[3,4-b]pyrazin-7-yl)car bamates," J Med Chem. 32(10):2363-7 (1989).
Terao et al., "Synthesis of .alpha.-thio, .alpha.-sulfinyl, and .alpha.-sulfonyl-substituted nitrosamines," Chem Pharm Bull. 25(11):2964-8 (1977).
Thalhamer et al., "MAPKs and their relevance to arthritis and inflammation," Rheumatology (Oxford). 47(4):409-414 (2008).
Thornber, "Isosterism and molecular modification in drug design," Chem Soc Rev. 8(4):563-80 (1979).
Uchida et al., "Studies on 2(1H)-quinolinone derivatives as gastric antiulcer active agents. 2-(4-chlorobenzoylamino)-3-[2(1H)-quinolinon-4-yl]propionic acid and related compounds," Chem Pharm Bull (Tokyo). 33(9):3775-86 (1985).
Vergani et al., "Identification of MET and SRC activation in melanoma cell lines showing primary resistance to PLX4032," Neoplasia. 13(12):1132-1142 (2011) (14 pages).
Villanueva et al., "Acquired resistance to BRAF inhibitors mediated by a RAF kinase switch in melanoma can be overcome by cotargeting MEK and IGF-1R/PI3K," Cancer Cell. 18(6):683-695 (2010) (34 pages).
Wan et al., "Mechanism of activation of the RAF-ERK signaling pathway by oncogenic mutations of B-RAF," Cell. 116(6):855-67 (2004).
Wang et al., "Antisense targeting of basic fibroblast growth factor and fibroblast growth factor receptor-1 in human melanomas blocks intratumoral angiogenesis and tumor growth," Nat Med. 3(8): 887-93 (1997).
Wang et al., "Inhibition of MEK/ERK ½ pathway reduces pro-inflammatory cytokine interleukin-1 expression in focal cerebral ischemia," Brain Res. 996(1):55-66 (2004).
Wang et al., "Molecular distinction and angiogenic interaction between embryonic arteries and veins revealed by ephrin-B2 and its receptor Eph-B4", Cell. 93(5):741-53 (1998).
Wang et al., "Significant neuroprotection against ischemic brain injury by inhibition of the MEK1 protein kinase in mice: exploration of potential mechanism associated with apoptosis," J Pharmacol Exp Ther. 304(1): 172-178 (2003).
Ward et al., "Targeting oncogenic Ras signaling in hematologic malignancies," Blood. 120(17): 3397-3406 (2012).
Wellbrock et al., "The RAF proteins take centre stage," Nat Rev Mol Cell Biol. 5(11):875-85 (2004).
Wellbrock et al., "V599EB-RAF is an oncogene in melanocytes," Cancer Res. 64(7): 2338-2342 (2004) (6 pages).
Whittaker et al., "A novel, selective and efficacious nanomolar pyridopyrazinone inhibitor of V600EBRAF," Cancer Res. 70(20): 8036-8044 (2010) (13 pages).
Wilks, "Structure and function of the protein tyrosine kinases," Prog Growth Factor Res. 2(2):97-111 (1990).
Wilson et al., "Widespread potential for growth-factor-driven resistance to anticancer kinase inhibitors," Nature. 487(7408): 505-509 (2012) (6 pages).
Xing, "Molecular pathogenesis and mechanisms of thyroid cancer," Nat Rev Cancer. 13(3):184-199 (2013).
Yancopoulos et al., "Vasculogenesis, angiogenesis and growth factors: ephrins enter the fray at the border," Cell. 93(5):661-4 (1998).
Yang et al., "Regulation of human immunodeficiency virus type 1 infectivity by the ERK mitogen-activated protein kinase signaling pathway," J Virol. 73(4):3460-3466 (1999).

(56) References Cited

OTHER PUBLICATIONS

Yao et al., "Lipopolysaccharide induction of the tumor necrosis factor-alpha promoter in human monocytic cells. Regulation by Egr-1, c-Jun and NF-kappaB transcription factors," J Biol Chem. 272(28): 17795-17801 (1997).

Yeatman, "A renaissance for SRC," Nat Rev Cancer. 4(6):470-480 (2004).

Young et al., "Ras signaling and therapies," Adv Cancer Res. 102:1-17 (2009).

Yu et al., "Loss of fibroblast growth factor receptor 2 ligand-binding specificity in Apert syndrome," Proc Natl Acad Sci U.S.A. 97(26):14536-41 (2000).

Zambon et al., "Novel hinge binder improves activity and pharmacokinetic properties of BRAF inhibitors," J Med Chem. 53(15):5639-55 (2010).

Zejc et al., "Synthesis and anticonvulsant properties of some arylsuccinate methylpyridylimides", Pol J Pharmacol Pharm. 42(1):69-77 (1990).

Zhang et al., "Activation of the Ras/Raf/MEK pathway facilitates hepatitis C virus replication via attenuation of the interferon-JAK-STAT pathway," J Virol. 86(3): 1544-1554 (2012).

Zhang et al., "Targeting Src family kinases in anti-cancer therapies: turning promise into triumph," Trends Pharmacol Sci. 33(3): 122-128 (2012).

Zhou et al.,"Synthesis and SAR of 5-, 6-, 7- and 8-aza analogues of 3-aryl-4-hydroxyquinolin-2(1H)-one as NMDA/glycine site antagonists," Bioorg Med Chem. 9(8):2061-2071 (2001).

Ziegler et al.,"Some 9-Aza-alloxazines," J Am Chem Soc. 71:1891-1893 (1949).

Zouki et al.,"Peroxynitrite induces integrin-dependent adhesion of human neutrophils to endothelial cells via activation of the Raf-1/MEK/Erk pathway," FASEB J. 15(1):25-27 (2001).

PROCESS FOR THE PREPARATION OF 8-(4-AMINOPHENOXY)-4H-PYRIDO[2,3-B]PYRAZIN-3-ONE DERIVATIVES

CROSS-REFERENCE TO RELATED APPLICATIONS

This application is a National Stage Application of PCT/GB2014/053489 filed Nov. 25, 2014, which claims priority from UK Patent Application No. 1320732.9, filed on Nov. 25, 2013. Each of the prior mentioned applications is hereby incorporated by reference herein in its entirety.

RELATED APPLICATION

This application is related to: United Kingdom patent application number 1320732.9 filed 25 Nov. 2013, the contents of which are incorporated herein by reference in their entirety.

TECHNICAL FIELD

The present invention pertains generally to the field of organic chemical synthesis, and in particular to certain methods for the synthesis of 8-(4-aminophenyoxy)-4H-pyrido[2,3-b]pyrazin-3-one and related compounds (denoted herein as (3)) from 4-(4-aminophenyoxy)pyridine-2, 3-diamine and related compounds (denoted herein as (1)), by reaction with glyoxylic acid (denoted herein as (2)). The compounds (3) are useful in the synthesis of known anticancer agents, such as 1-(5-tert-butyl-2-(4-methyl-phenyl)-pyrazol-3-yl)-3-[2-fluoro-4-[(3-oxo-4H-pyrido[2,3-b]pyrazin-8-yl)oxy]phenyl]urea.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Springer et al., 2009, describes certain compounds including, for example, compound AA-018 shown below, which are useful, for example, in the treatment of cancer.

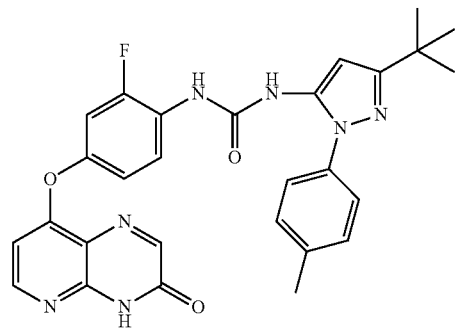 [SMILES: Cc1ccc(-n2nc(C(C)(C)C)cc2NC(=O)Nc2ccc(Oc3ccnc4[nH]c(=O)cnc34)cc2F)cc1]

1-(5-tert-butyl-2-(4-methyl-phenyl)-pyrazol-3-yl)-3-[2-fluoro-4-[(3-oxo-4H-pyrido[2, 3-b]pyrazin-8-yl)oxy]phenyl]urea (AA-018)

Springer et al., 2009 also describes methods of preparing such compounds. As part of those methods, the 3-oxo-4H-pyrido[2,3-b]pyrazin-8-yl group is formed in a mixture of two regioisomers (the 2-oxo and 3-oxo regioisomers) by a cyclisation reaction of a 2,3-diamino-4-oxy-pyridyl compound with ethyl glyoxylate, as illustrated in the following scheme (drawn from Synthesis 27 therein).

Scheme 1

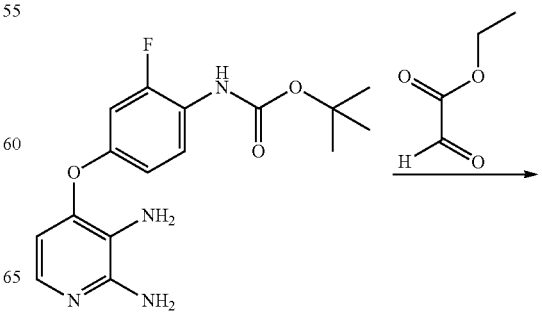

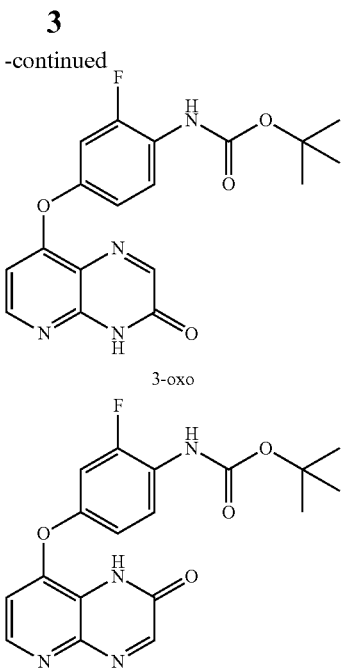

3-oxo 2-oxo

The method used in Synthesis 27 therein is described as: "Using Method D1 with tert-butyl 4-(2,3-diaminopyridin-4-yloxy)-2-fluorophenyl carbamate (3.50 g, 10.5 mmol), tert-butyl 2-fluoro-4-(2-oxo-1,2-dihydropyrido[2,3-b]pyrazin-8-yloxy) phenyl carbamate (2.71 g, 69%) and tert-butyl 2-fluoro-4-(3-oxo-1,2-dihydropyrido[2,3-b]pyrazin-8-yloxy) phenyl carbamate (0.96 g, 25%) were obtained."

For reference, "Method D1" is described in the context of Synthesis 25 therein as: "tert-butyl 4-(2,3-diaminopyridin-4-yloxy)phenylcarbamate (0.86 g, 2.71 mmol) was dissolved in 15 ml of dry ethanol; 0.8 ml (4 mmol) of a 50% ethyl glyoxylate solution in toluene were added and the solution was stirred overnight at room temperature under Argon atmosphere. The solvent was partially evaporated, and tert-butyl 4-(2-oxo-1,2-dihydropyrido[2,3-b]pyrazin-8-yloxy)phenylcarbamate (0.430 g, 45% yield) is precipitated by addition of acetone (10 ml) and filtered off."

Such cyclisation methods suffer from low yield. In addition, both regioisomers are formed, and the undesired regioisomer ("2-oxo") is formed preferentially. Furthermore, the purification of the desired regioisomer ("3-oxo") away from the undesired regioisomer can be difficult and may require extensive column chromatography.

Reported yields for the reaction are summarised in the following table.

| Compound | Reported Yield | Citation |
|---|---|---|
|  | 21% | Springer et al., 2009 (Synthesis 24) (pages 104-105) |
|  | 25% | Springer et al., 2009 (Synthesis 27) (pages 106-107) |
|  | 15% | Springer et al., 2009 (Synthesis 26) (pages 105-106) |
|  | 7%[1] | Zambon et al., 2010 (Compound 7h) (page S8) |
|  | 24% | Murray et al. 2011 (Intermediate D2) (page 44) |

(1) Note that there is an error in the publication; the reported yield of 240 mg corresponds to a 7% yield, not a 9% yield.

As described herein, the present inventors have determined that the synthetic method can be very greatly improved (e.g., higher yield; preferential formation of desired regioisomer) by employing a different reagent (i.e., glyoxylic acid), especially under certain reaction conditions, including, in particular, a large excess of glyoxylic acid (i.e., a molar excess of at least about 2).

Cyclisation Using Glyoxylic Acid

The use of glyoxylic acid in methanol for the synthesis of the pyridopyrazinone bicyclic system has been reported in a limited number of publications. In each case, the pyridopyrazinone compounds synthesised were either unsubstituted on the pyridyl ring, or substituted with halogen at the 5-position of the pyridyl ring.

Bekerman et al., 1992, describes the reaction of unsubstituted 2,3-daminopyridine with glyoxylic acid and derivatives in a number of solvents. In methanol, the reaction constant for the undesired regioisomer ("2-oxo") is higher than the reaction constant for the desired regioisomer ("3-oxo"). In chloroform, the ratio is even higher in favour of the undesired regioisomer. In aqueous media, the desired regioisomer is formed preferentially; however, these conditions are not suitable for water insoluble compounds.

Milbank et al., 2011, describes the synthesis of 7-bromopyrido[2,3-b]pyrazin-3(4H)-one from 5-bromopyridine-2,3-diamine and glyoxylic acid in methanol. However, the isomers were obtained as a mixture and were not separated.

Ballell et al., 2008, describes the same synthesis in water, where the undesired 7-bromopyrido[2,3-b]pyrazin-2(1H)-one is obtained as the major isomer in 66% yield. Similarly, the undesired 7-fluoropyrido[2,3-b]pyrazin-2(1H)-one was obtained as the major isomer in 54% yield.

To date, there has been no report of the use of a corresponding method for the synthesis of 4-substituted pyrido[2,3-b]pyrazin-2(1H)-ones. Therefore, the regioselectivity of the cyclisation reaction could not have been predicted with reasonable certainty. Furthermore, the high regioselectivity demonstrated by the inventors and described herein is surprising and unexpected.

Additional publications which describe the use of glyoxylic acid or a glyoxylic acid ester for cyclisation include the following: Abosolo et al., 1990; Bates et al., 1990; Bergman et al., 1996; Clark-Lewis et al., 1957; Cushman et al., 1992; Dettner et al., 1996; Dubey et al., 2001; Leese et al., 1955; Mashelkar et al., 2006; McKillop et al., 1997; Reck et al., 2011; Remli et al., 1989; Rudy et al., 1938; Seki et al., 1995; Sherman et al., 2007; Ziegler et al., 1949.

SUMMARY OF THE INVENTION

One aspect of the invention pertains to a method of preparing a compound of Formula (3), as described herein:

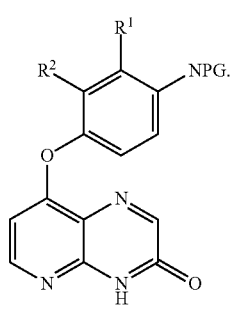

(3)

Another aspect of the present invention pertains to a compound of Formula (3) obtained by a method of synthesis as described herein, or a method comprising a method of synthesis as described herein.

Another aspect of the invention pertains to method of chemical synthesis which include, as part of the chemical synthesis, a method of preparing a compound of Formula (3), as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

The present inventors have determined that the synthesis of 8-(4-aminophenyoxy)-4H-pyrido[2,3-b]pyrazin-3-one and related compounds (denoted herein as (3)) from 4-(4-aminophenyoxy)pyridine-2,3-diamine and related compounds (denoted herein as (1)) can be very greatly improved (e.g., higher yield; preferential formation of the desired regioisomer) by employing a different reagent (i.e., glyoxylic acid; denoted herein as (2)) under certain reaction conditions, including, in particular, a large excess of glyoxylic acid (i.e., a molar excess of at least about 2).

Cyclization Step

One aspect of the present invention is a method of preparing a compound of Formula (3):

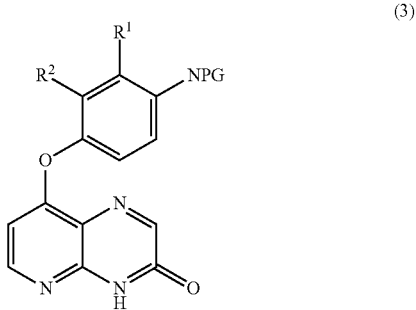

(3)

comprising reacting a compound of Formula (1):

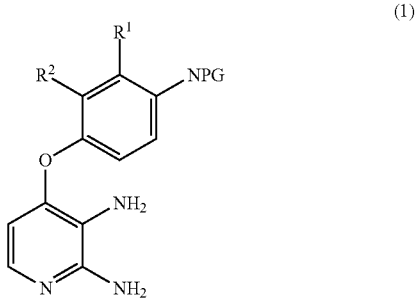

(1)

with a compound of Formula (2):

(2)

in a reaction mixture under cyclisation conditions to form said compound of Formula (3);
wherein the ratio of the amount of the compound of Formula (2) to the amount of the compound of Formula (1), on a molar basis, is at least about 2; and wherein:
—R¹ is independently —H or —R¹ᴬ;
—R² is independently —H or —R²ᴬ;
—R¹ᴬ is independently —F, —Cl, —Br, —I, —Rˣ, —OH, —ORˣ, or —SRˣ;
—R²ᴬ is independently —F, —Cl, —Br, —I, —Rˣ, —OH, —ORˣ, or —SRˣ;
each —Rˣ is independently linear or branched saturated $C_{1-4}$alkyl;
or —R¹ and —R₂ together form —CH=CH—CH=CH—, —N=CH—CH=CH—, —CH=N—CH=CH—, —CH=CH—N=CH—, or —CH=CH—CH=N—; and
—NPG is a protected amino group which is stable to said cyclisation conditions.

Note that tautomerisation is possible on the 3-oxo-3,4-dihydropyrido[3,2-b]pyrazin-8-yl group of compounds of Formula (3), as shown below. Unless otherwise indicated, a reference to one tautomer is intended to be a reference to both tautomers.

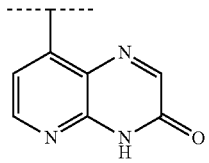

is a tautomer of

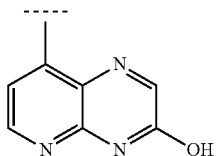

For the avoidance of doubt: n-propyl is abbreviated as -nPr; iso-propyl is abbreviated as -iPr; n-butyl is abbreviated as -nBu; iso-butyl is abbreviated as -iBu; sec-butyl is abbreviated as -sBu; tert-butyl is abbreviated as -tBu; and phenyl is abbreviated as -Ph.

The Group —R¹
In one embodiment, —R¹ is —H.
In one embodiment, —R¹ is —R¹ᴬ.

The Group —R²
In one embodiment, —R² is —H.
In one embodiment, —R² is —R²ᴬ.

The Group —R¹ᴬ
In one embodiment, —R¹ᴬ, if present, is independently —F, —Cl, —Br, or —I;
In one embodiment, —R¹ᴬ, if present, is —F.
In one embodiment, —R¹ᴬ, if present, is —Cl.
In one embodiment, —R¹ᴬ, if present, is —Br.
In one embodiment, —R¹ᴬ, if present, is —I.
In one embodiment, —R¹ᴬ, if present, is independently —OH or —ORˣ.
In one embodiment, —R¹ᴬ, if present, is —OH.
In one embodiment, —R¹ᴬ, if present, is —ORˣ.
In one embodiment, —R¹ᴬ, if present, is —SRˣ.

The Group —R²ᴬ
In one embodiment, —R²ᴬ, if present, is independently —F, —Cl, —Br, or —I;
In one embodiment, —R²ᴬ, if present, is —F.
In one embodiment, —R²ᴬ, if present, is —Cl.
In one embodiment, —R²ᴬ, if present, is —Br.
In one embodiment, —R²ᴬ, if present, is —I.
In one embodiment, —R²ᴬ, if present, is independently —OH or —ORˣ.
In one embodiment, —R²ᴬ, if present, is —OH.
In one embodiment, —R²ᴬ, if present, is —ORˣ.
In one embodiment, —R²ᴬ, if present, is —SRˣ.

The Group —Rˣ
In one embodiment, each —Rˣ, if present, is independently -Me, -Et, -nPr, -iPr, -nBu, -iBu, -sBu, or -tBu.
In one embodiment, each —Rˣ, if present, is independently -Me, -Et, -nPr, or -iPr.
In one embodiment, each —Rˣ, if present, is independently -Me or -Et.
In one embodiment, each —Rˣ, if present, is -Me.

The Group —R¹ and —R² Taken Together
In one embodiment, —R¹ and —R₂ together form —CH=CH—CH=CH—, —N=CH—CH=CH—, —CH=N—CH=CH—, —CH=CH—N=CH—, or —CH=CH—CH=N—.
In one embodiment, —R¹ and —R₂ together form —CH=CH—CH=CH—, for example, as in:

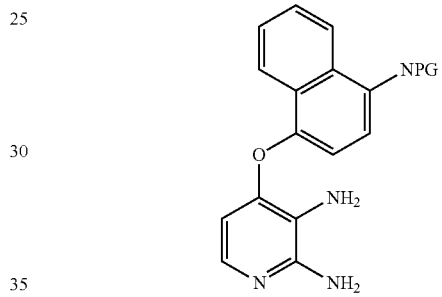

In one embodiment, —R¹ and —R₂ together form —N=CH—CH=CH—, —CH=N—CH=CH—, —CH=CH—N=CH—, or —CH=CH—CH=N—.

The Protected Amino Group -NPG
The protected amino group, -NPG, is a protected amino group which is stable to said cyclisation conditions.

For example, the protected amino group, -NPG, is a protected amino group which is stable to mildly acidic conditions (e.g., glyoxylic acid in organic solvent, e.g., MeOH) and unreactive for nucleophilic addition towards a carbonyl group (e.g., the aldehyde moiety of glyoxylic acid and ethyl glyoxylate). A wide range of examples of suitable protecting groups (including methods for their formation and subsequent deprotection) can be found, for example, in Protective Groups in Organic Synthesis (T. Greene and P. Wuts; 4th Edition; John Wiley and Sons, 2006) and Protecting Groups (Philip J. Kocienski; Thieme, 2005).

In one embodiment, -NPG is independently a protected amino group in the form of: a carbamate; an amide; an imide; or a sulfonamide.

| —NPG | Example |
|---|---|
| a carbamate | |

| —NPG | Example |
|---|---|
| an amide | a structure showing —NH—C(=O)—CF₃ |
| an imide | a phthalimide structure (N bonded to two C=O of a benzene-fused ring) |
| a sulfonamide | a structure showing —NH—S(=O)₂—C₆H₄—CH₃ (tosyl) |

In one embodiment, -NPG is a protected amino group in the form of a carbamate.

In one embodiment, -NPG is independently:
methyl carbamate;
ethyl carbamate;
9-fluorenylmethyl carbamate (Fmoc-NR2);
9-(2,7-dibromo)fluorenylmethyl carbamate;
2-chloro-3-indenylmethyl carbamate (Climoc-NR2);
benz[f]inden-3-ylmethyl carbamate (Bimoc-NR2);
2,7-Di-t-Butyl[9-(10,10-dioxo-10,10,10-tetrahydrothi-oxanthyl)]methyl carbamate (DBD-Tmoc-NR2);
2-trimethylsilylethyl carbamate (Teoc-NR2)
2,2,2-trichloroethyl carbamate;
1,1-dimethylpropynyl carbamate;
1,1-dimethyl-2-haloethyl carbamate;
1,1-dimethyl-2-cyanoethyl carbamate;
t-butyl carbamate;
cyclobutyl carbamate;
vinyl carbamate;
8-quinolyl carbamate;
N-hydroxypiperidinyl carbamate;
4,5-diphenyl-3-oxazolin-2-one;
benzyl carbamate (Cbz-NR2);
p-nitrobenzyl carbamate;
3,4-dimethoxy-6-nitrobenzyl carbamate;
2,4-dichlorobenzyl carbamate;
5-benzisoxazolylmethyl carbamate;
9-anthrylmethyl carbamate;
isonicotinyl carbamate; or
S-benzyl carbamate.

In one embodiment, -NPG is t-butyl carbamate.

In one embodiment, -NPG is a protected amino group in the form of an amide.

In one embodiment, -NPG is independently:
N-formyl amide;
N-acetyl amide;
N-chloroacetyl amide;
N-trichloroacetyl amide;
N-trifluoroacetyl amide;
N-o-nitrophenylacetyl amide;
N-o-nitrophenoxyacetyl amide;
N-3-phenylpropionyl amide;
N-3-(p-hydroxyphenyl)propionyl amide;
N-2-methyl-2-(o-phenylazophenoxy)propionyl amide;
N-4-chlorobutyryl amide;
N-o-nitrocinnamoyl amide;
N-picolinoyl amide;
N—(N'-acetylmethionyl) amide; or
N-benzoyl amide.

In one embodiment, -NPG is a protected amino group in the form of an imide.

In one embodiment, -NPG is independently:
N-phthalimide;
N-tetrachlorophthalimide;
4-nitro-N-phthalimide;
N-2,3-diphenylmaleimide; or
N-dithiasuccinoylimide.

In one embodiment, -NPG is a protected amino group in the form of a sulfonamide.

In one embodiment, -NPG is independently:
p-toluenesulfonamide; or
benzenesulfonamide.

In one embodiment, -NPG is a protected amino group which, additionally, is stable to strong basic conditions (e.g., $K_2CO_3$ in DMF) and reductive conditions (e.g., $H_2$ on Pd/C). An example of such a group is tert-butyl carbamate.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by variables (e.g., —$R^1$, —$R^{1A}$, —$R^2$, —$R^{2A}$, —$R^X$, —NPG, -A, —Ar, —Y, -$A^1$, -$A^2$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Glyoxylic Acid

The compound of Formula (2) is glyoxylic acid.

Glyoxylic acid (also known as oxoacetic acid; oxoethanoic acid; and formylformic acid) has the chemical formula $OCHCO_2H$ and a molecular weight of 74.04 g/mol. It is often handled as the monohydrate, $OCHCO_2H \cdot H_2O$, which has a molecular weight of 92.05 g/mol. Both are solids at room temperature.

Excess of Glyoxylic Acid

In one embodiment, the ratio of the amount of the compound of Formula (2) to the amount of the compound of Formula (1), on a molar basis, is at least about 2.

In one embodiment, the ratio is from about 2 to about 25.
In one embodiment, the ratio is from about 2 to about 20.
In one embodiment, the ratio is from about 2 to about 15.
In one embodiment, the ratio is from about 2 to about 10.
In one embodiment, the ratio is from about 5 to about 25.
In one embodiment, the ratio is from about 5 to about 20.
In one embodiment, the ratio is from about 5 to about 15.
In one embodiment, the ratio is from about 5 to about 10.
In one embodiment, the ratio is about 10.

Slow Rate of Addition

In one embodiment, the compound of Formula (1) and the compound of Formula (2) are combined over an addition time of at least about 30 minutes to form the reaction mixture.

For the avoidance of doubt, the term "over" in the phrase "over an addition time" is used in this context to mean that the combining occurs substantially continuously throughout substantially all of the duration of the addition time; the term is intended to include, for example, dropwise addition, continuous flow addition, etc.

In one embodiment, the addition time is from about 30 minutes to about 24 hours.

In one embodiment, the addition time is from about 1 hour to about 24 hours.

In one embodiment, the addition time is from about 2 hours to about 24 hours.

In one embodiment, the addition time is from about 3 hours to about 24 hours.

In one embodiment, the addition time is from about 30 minutes to about 18 hours.

In one embodiment, the addition time is from about 1 hour to about 18 hours.

In one embodiment, the addition time is from about 2 hours to about 18 hours.

In one embodiment, the addition time is from about 3 hours to about 18 hours.

In one embodiment, the addition time is from about 30 minutes to about 12 hours.

In one embodiment, the addition time is from about 1 hour to about 12 hours.

In one embodiment, the addition time is from about 2 hours to about 12 hours.

In one embodiment, the addition time is from about 3 hours to about 12 hours.

In one embodiment, the addition time is from about 30 minutes to about 6 hours.

In one embodiment, the addition time is from about 1 hour to about 6 hours.

In one embodiment, the addition time is from about 2 hours to about 6 hours.

In one embodiment, the addition time is from about 3 hours to about 6 hours.

In one embodiment, the addition time is about 30 minutes.

In one embodiment, the addition time is about 1 hour.

In one embodiment, the addition time is about 2 hours.

In one embodiment, the addition time is about 3 hours.

In one embodiment, the addition time is about 6 hours.

Further Reaction Time

In one embodiment, after the compound of Formula (1) and the compound of Formula (2) have been combined (e.g., after the addition time), the reaction is allowed to continue for a further reaction time, for example, at the reaction temperature, optionally with stirring (i.e., of the reaction mixture).

In one embodiment, the further reaction time is from about 1 hour to about 48 hours.

In one embodiment, the further reaction time is from about 1 hour to about 36 hours.

In one embodiment, the further reaction time is from about 1 hour to about 24 hours.

In one embodiment, the further reaction time is from about 1 hour to about 12 hours.

In one embodiment, the further reaction time is from about 3 hours to about 48 hours.

In one embodiment, the further reaction time is from about 3 hours to about 36 hours.

In one embodiment, the further reaction time is from about 3 hours to about 24 hours.

In one embodiment, the further reaction time is from about 3 hours to about 12 hours.

In one embodiment, the further reaction time is from about 6 hours to about 48 hours.

In one embodiment, the further reaction time is from about 6 hours to about 36 hours.

In one embodiment, the further reaction time is from about 6 hours to about 24 hours.

In one embodiment, the further reaction time is from about 6 hours to about 12 hours.

In one embodiment, the reaction mixture is stirred during the further reaction time.

Reaction Solvent

In one embodiment, the reaction mixture further comprises a reaction solvent.

In one embodiment, the reaction solvent is an organic solvent.

In one embodiment, the reaction solvent is an aprotic organic solvent.

In one embodiment, the reaction solvent is, or comprises, an organic nitrile (e.g., acetonitrile).

In one embodiment, the reaction solvent is, or comprises, an organic ester (e.g., ethyl acetate).

In one embodiment, the reaction solvent is, or comprises, a sulfoxide (e.g., dimethylsulfoxide (DMSO)).

In one embodiment, the reaction solvent is, or comprises, an organic amide (e.g., dimethylformamide (DMF), dimethylacetamide (DMA), N-methyl-2-pyrrolidone (NMP), or a mixture of thereof).

In one embodiment, the reaction solvent is, or comprises, an aromatic organic solvent (e.g., toluene, xylene, or a mixture thereof).

In one embodiment, the reaction solvent is, or comprises, a linear or branched ether (e.g., diethyl ether, tert-butyl methyl ether, or a mixture of thereof).

In one embodiment, the reaction solvent is, or comprises, a cyclic ether (e.g., tetrahydrofuran (THF)).

In one embodiment, the reaction solvent is, or comprises, an alcohol.

In one embodiment, the reaction solvent is, or comprises, a $C_{1-6}$alkyl alcohol, or a mixture of two or more $C_{1-4}$alkyl alcohols.

In one embodiment, the reaction solvent is, or comprises, a $C_{1-4}$alkyl alcohol, or a mixture of two or more $C_{1-4}$alkyl alcohols.

In one embodiment, the reaction solvent is, or comprises, MeOH, EtOH, or THF, or a mixture thereof.

In one embodiment, the reaction solvent is MeOH, EtOH, or THF, or a mixture thereof.

In one embodiment, the reaction solvent is, or comprises, MeOH, EtOH, or a mixture of MeOH and EtOH.

In one embodiment, the reaction solvent is MeOH, EtOH, or a mixture of MeOH and EtOH.

In one embodiment, the reaction solvent is MeOH.

In one embodiment, the reaction solvent is EtOH.

In one embodiment, the reaction solvent is THF.

Amount of Solvent

In one embodiment, the volume of reaction solvent in the reaction mixture is from about 5 to about 50 L per kg of compound of Formula (1).

More specifically, in the above embodiment, the volume of reaction solvent, measured in litres, is from about 5 to about 50 times the weight of the compound of Formula (1), measured in kilograms.

In one embodiment, the volume of reaction solvent in the reaction mixture is from about 10 to about 30 L per kg of compound of Formula (1).

In one embodiment, the volume of reaction solvent in the reaction mixture is from about 15 to about 25 L per kg of compound of Formula (1).

In one embodiment, the volume of reaction solvent in the reaction mixture is about 20 L per kg of compound of Formula (1).

When the compound of Formula (1) is tert-butyl N-[4-[(2,3-diamino-4-pyridyl)oxy]-2-fluoro-phenyl]carbamate, which has an empirical formula of $C_{16}H_{19}FN_4O_3$ and a molecular weight of 334.34 g/mol, one kilogram contains about 3 moles of compound of Formula (1). Consequently, when the volume of reaction solvent is from about 5 to about 50 L per kg of compound of Formula (1), the concentration of the compound of Formula (1) in the reaction mixture is from about 3 mol/5 L to about 3 mol/50 L, or from about 0.6 to about 0.06 M. Similarly, when the volume of reaction solvent is about 20 L per kg of compound of Formula (1), the concentration of the compound of Formula (1) in the reaction mixture is from about 3 mol/20 L or about 0.15 M. (In this context, the concentration in the reaction mixture is the theoretical concentration based on the amount of compound of Formula (1) and the amount of solvent used to form the reaction mixture, rather than any actual instantaneous concentration of the compound of Formula (1) in the reaction mixture during the reaction process.)

In one embodiment, the concentration of the compound of Formula (1) in the reaction mixture is from about 0.01 to about 1 M.

In one embodiment, the concentration of the compound of Formula (1) in the reaction mixture is from about 0.02 to about 0.5 M.

In one embodiment, the concentration of the compound of Formula (1) in the reaction mixture is from about 0.05 to about 0.3 M.

In one embodiment, the concentration of the compound of Formula (1) in the reaction mixture is from about 0.05 to about 0.2 M.

In one embodiment, the concentration of the compound of Formula (1) in the reaction mixture is about 0.10 M.

In one embodiment, the concentration of the compound of Formula (1) in the reaction mixture is about 0.15 M.

Methods of Combining

In one embodiment, the compound of Formula (1) is dissolved in a first solvent to form a starting material solution before being combined with the compound of Formula (2) to form the reaction mixture, wherein said first solvent is, or forms part of, the reaction solvent.

In one embodiment, the compound of Formula (2) is dissolved in a second solvent to form a glyoxylic acid reagent solution before being combined with the compound of Formula (1) to form the reaction mixture, wherein said first solvent is, or forms part of, the reaction solvent.

In one embodiment:
the compound of Formula (1) is dissolved in a first solvent to form a starting material solution before being combined with the compound of Formula (2) to form the reaction mixture, wherein said first solvent forms part of the reaction solvent; and
the compound of Formula (2) is dissolved in a second solvent to form a glyoxylic acid reagent solution before being combined with the compound of Formula (1) to form the reaction mixture, wherein said second solvent forms part of the reaction solvent.

In one embodiment, the first solvent and the second solvent, if both present, are the same (e.g., both methanol).

In one embodiment, the first solvent and the second solvent, if both present, are different.

In one embodiment, said starting material solution is combined with said glyoxylic acid reagent solution by adding said starting material solution to said glyoxylic acid reagent solution.

In one embodiment, said starting material solution is combined with said glyoxylic acid reagent solution by adding said glyoxylic acid reagent solution to said starting material solution.

In one embodiment, said adding (i.e., adding said starting material solution to said glyoxylic acid reagent solution; adding said glyoxylic acid reagent solution to said starting material solution) is adding continuously (e.g., over the addition time).

In one embodiment, said adding is adding continuously is by dropwise addition.

In one embodiment, said adding is adding continuously is by continuous flow addition.

In one embodiment, the compound of Formula (2) is added as a solid to said starting material solution.

In one embodiment, the compound of Formula (2) is added as a solid to said starting material solution continuously (e.g., over the addition time).

In one embodiment, the compound of Formula (1) is added as a solid to said glyoxylic acid reagent solution.

In one embodiment, the compound of Formula (1) is added as a solid to said glyoxylic acid reagent solution continuously (e.g., over the addition time).

Reaction Temperature

In one embodiment, the temperature of the reaction mixture during the reaction is, or is maintained at, a temperature of from about 0° C. to about the reflux temperature of the reaction mixture.

In one embodiment, the temperature of the reaction mixture during the reaction is a temperature of from about 0° C. to about the reflux temperature of the reaction mixture.

In one embodiment, the temperature of the reaction mixture during the reaction is maintained at a temperature of from about 0° C. to about the reflux temperature of the reaction mixture.

In one embodiment, the temperature range is from about 0° C. to about 78° C.

In one embodiment, the temperature range is from about 0° C. to about 30° C.

In one embodiment, the temperature range is from about 0° C. to about 25° C.

In one embodiment, the temperature range is from about 5° C. to about 30° C.

In one embodiment, the temperature range is from about 5° C. to about 25° C.

In one embodiment, the temperature range is from about 10° C. to about 30° C.

In one embodiment, the temperature range is from about 10° C. to about 25° C.

In one embodiment, the temperature range is from about 15° C. to about 25° C.

In one embodiment, the temperature is about 20° C.

Combinations

As discussed above, certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the reaction conditions (e.g., proportions of reagents; rate of addition of reagents; solvents; proportions of solvents; methods for combining reagents; temperature; etc.) are specifically embraced by the present invention and are disclosed herein just as if each and every combination was individually and explicitly disclosed, to the extent that such combinations are compatible. In addition, all sub-combinations of the reaction conditions listed in the embodiments describing such reaction conditions are also specifically embraced by the present invention and are disclosed herein just as if each and every such sub-combination of reaction conditions was individually and explicitly disclosed herein.

Optional Subsequent Steps

In one embodiment, the method further comprises a subsequent step (a "deprotection step") of deprotecting the protected amino group, for example, deprotecting a compound of Formula (3):

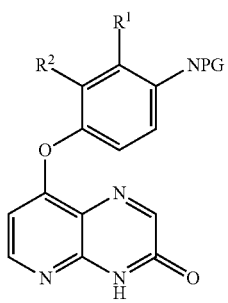

(3)

to give a compound of Formula (4):

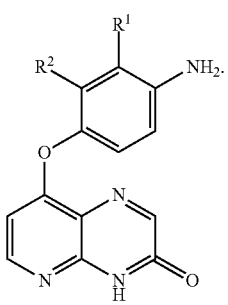

(4)

In one embodiment, the method further comprises a subsequent step (a "urea formation step") of reacting the resulting amino group with a suitable 5-activated-3-tert-butyl-1-aryl-pyrazole, for example, reacting a compound of Formula (4):

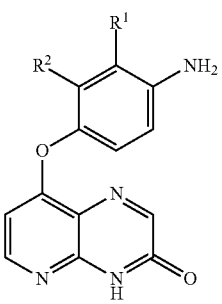

(4)

with a compound of Formula (5):

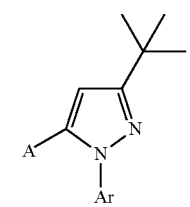

(5)

to give a compound of Formula (6):

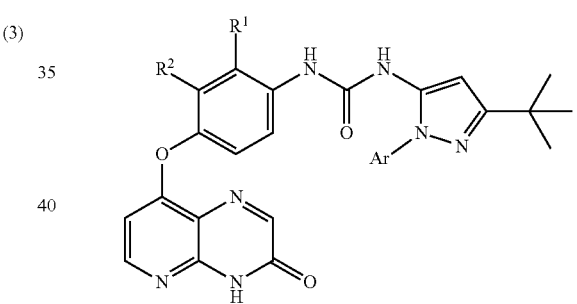

(6)

wherein:

-A is an activating group suitable for reaction with —NH$_2$ to form a urea group; and —Ar is phenyl, pyridyl, or naphthyl, and is optionally substituted with one or more groups —Y, wherein each —Y is independently selected from halo (e.g., —F, —Cl, —Br, or —I); linear or branched saturated C$_{1-4}$alkyl (e.g., -Me, -Et); linear or branched saturated C$_{1-4}$haloalkyl (e.g., —CF$_3$); —OH; linear or branched saturated C$_{1-4}$alkoxy (e.g., —OMe, —OEt); and linear or branched saturated C$_{1-4}$haloalkoxy (e.g., —OCF$_3$).

Alternatively, in one embodiment, the method further comprises subsequent steps (an "amino activation step" followed by a "urea formation step") of activating the resulting amino group, followed by reaction with a 5-amino-3-tert-butyl-1-aryl-pyrazole, for example, activating a compound of Formula (4):

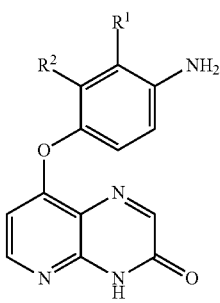

(4)

to give a compound of Formula (7):

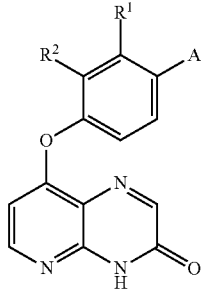

(7)

and the reacting the compound of Formula (7) with a compound of Formula (8):

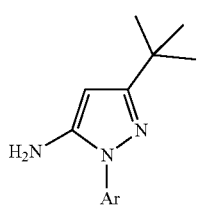

(8)

to give a compound of Formula (6):

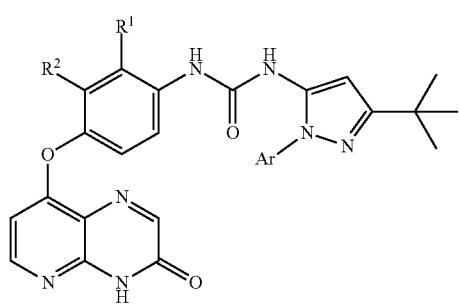

(6)

wherein:
-A is an activating group suitable for reaction with —NH$_2$ to form a urea group; and
—Ar is phenyl, pyridyl, or naphthyl, and is optionally substituted with one or more groups —Y, wherein each —Y is independently selected from halo (e.g., —F, —Cl, —Br, or —I); linear or branched saturated C$_{1-4}$alkyl (e.g., -Me, -Et); linear or branched saturated C$_{1-4}$haloalkyl (e.g., —CF$_3$); —OH; linear or branched saturated C$_{1-4}$alkoxy (e.g., —OMe, —OEt); and linear or branched saturated C$_{1-4}$haloalkoxy (e.g., —OCF$_3$).

In one embodiment, —Ar is phenyl or pyridyl, and is optionally substituted with one or more groups —Y.

In one embodiment, —Ar is phenyl, and is optionally substituted with one or more groups —Y.

In one embodiment, —Ar is phenyl, and is optionally substituted with one group —Y.

In one embodiment, —Ar is phenyl, and is optionally substituted with one group —Y at the meta-position (e.g., as shown below).

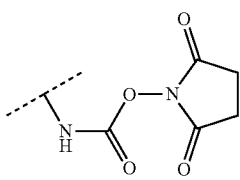

In one embodiment, —Ar is phenyl (i.e., unsubstituted phenyl).

In one embodiment, —Y (or each —Y, if there is more than one) is independently selected from —F, -Me, —CF$_3$, —OH, and —OMe.

In one embodiment, -A is a carbamate group (i.e., —NH—C(=O)OR).

In one embodiment, -A is —NH—C(=O)O-Ph.

In one embodiment, -A is —NH—C(=O)O-(4-nitrophenyl).

In one embodiment, -A is —NH—C(=O)O—C(CH$_3$)=CH$_2$.

In one embodiment, -A is —NH—C(=O)O—(N-succinimidyl) (shown below).

Suitable carbamates can be obtained, for example, by the reaction of the corresponding amine with a suitable chloroformate (e.g., phenyl chloroformate, 4-nitrophenyl chloroformate, 1-methylvinylchloroformate, etc.) or a suitable carbonate (e.g., N,N-disuccinimidyl carbonate).

In one embodiment, -A is an isocyanate group (i.e., —NCO).

Suitable isocyanates can be obtained, for example, by the conversion of the corresponding amine using, for example, phosgene, triphosgene, or their derivatives, or by conversion of the corresponding carboxylic acid to acyl azides using, for example, diphenyl phosphoryl azide, followed by a Curtius rearrangement.

Optional Preceding Steps

In one embodiment, the method further comprises a preceding step (a "nitro reduction step") of reducing a nitro group to form an amino group, for example, reducing a compound of Formula (9):

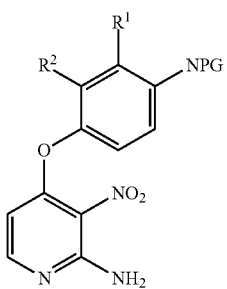

to give a compound of Formula (1):

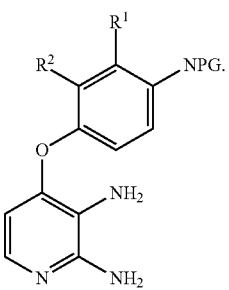

In one embodiment, the method further comprises a preceding step (a "coupling step") of coupling a suitable 4-activated-N-protected-aniline with a suitable 4-activated-2-amino-3-nitropyridine, for example, reacting a compound of Formula (10):

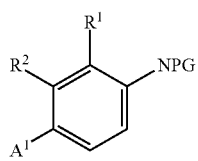

with a compound of Formula (11):

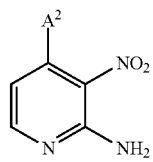

to give a compound of Formula (9):

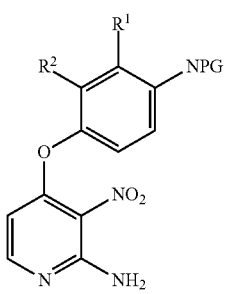

wherein -A$^1$ and -A$^2$ are activating groups suitable for reaction with each other to form an ether group, for example, in suitable reaction conditions.

In one embodiment, -A$^1$ is —OH.

In one embodiment, -A$^2$ is halogen (e.g., —F, —Cl, —Br, —I), cyano (i.e., —CN), acyloxy (e.g., —OC(=O)Me), sulfonate (e.g., —OS(=O)$_2$Me, —OS(=O)$_2$CF$_3$, —OS(=O)$_2$Ph, —OS(=O)$_2$(4-methylphenyl), etc.), sulfonyl (e.g., —S(=O)$_2$Me), sulfinyl (e.g., —S(=O)Me), nitro (i.e., —NO$_2$), a diazonium salt (i.e., —N(+)≡N), or an ammonium salt (e.g., —N(+)Me$_3$).

In one embodiment, -A$^1$ is —OH and -A$^2$ is halogen (e.g., —F, —Cl, —Br, —I).

In one embodiment, -A$^1$ is —OH and -A$^2$ is —Cl.

Multi-Step Synthesis

Thus, in one embodiment, the cyclisation method described herein forms part of a multi-step synthesis, as illustrated in the following schemes, to give target compounds which are useful, for example, as anti-cancer agents.

Scheme 2

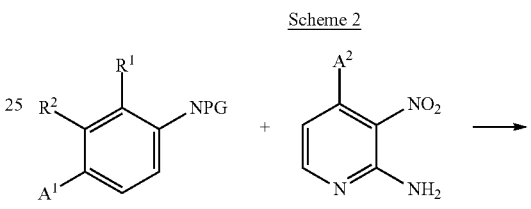

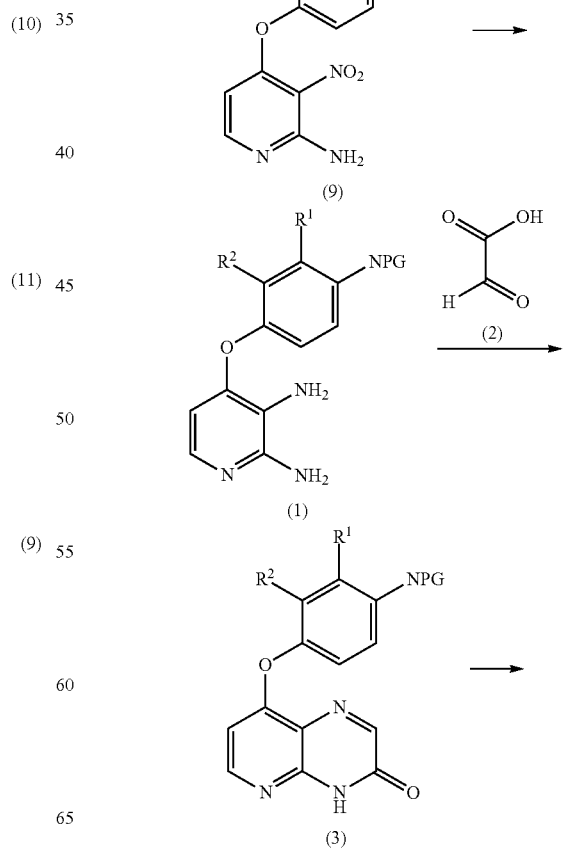

21
-continued
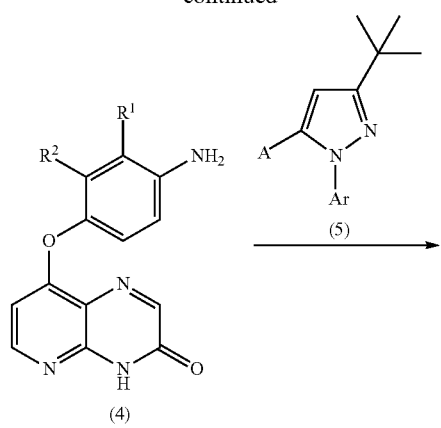
(4)
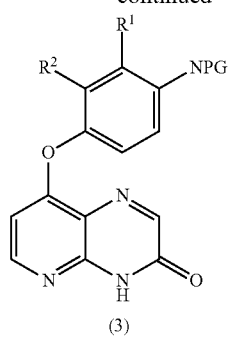
(6)
Scheme 3
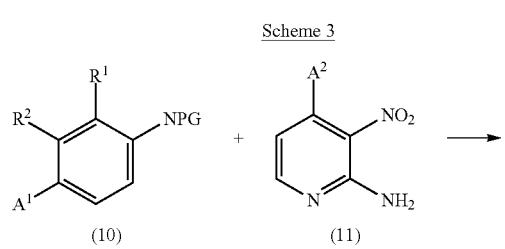
(9)
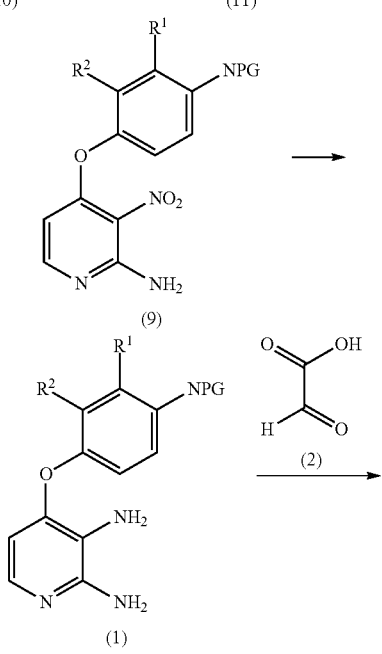
(1)
22
-continued
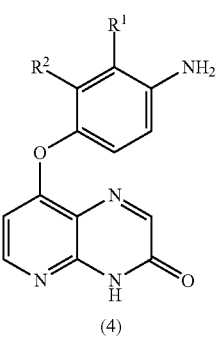
(3)
(4)
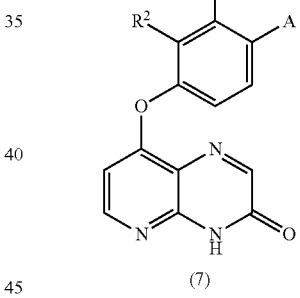
(7)
(6)
Detailed Study of Reaction Conditions
The synthetic step illustrated in the following scheme was studied in detail. SM denotes "starting material"; GA denotes "glyoxylic acid"; DR denotes desired regioiosmer (i.e., 3-oxo regioisomer); and UR denotes undesired regioisomer (i.e., 2-oxo regioisomer).

Scheme 4

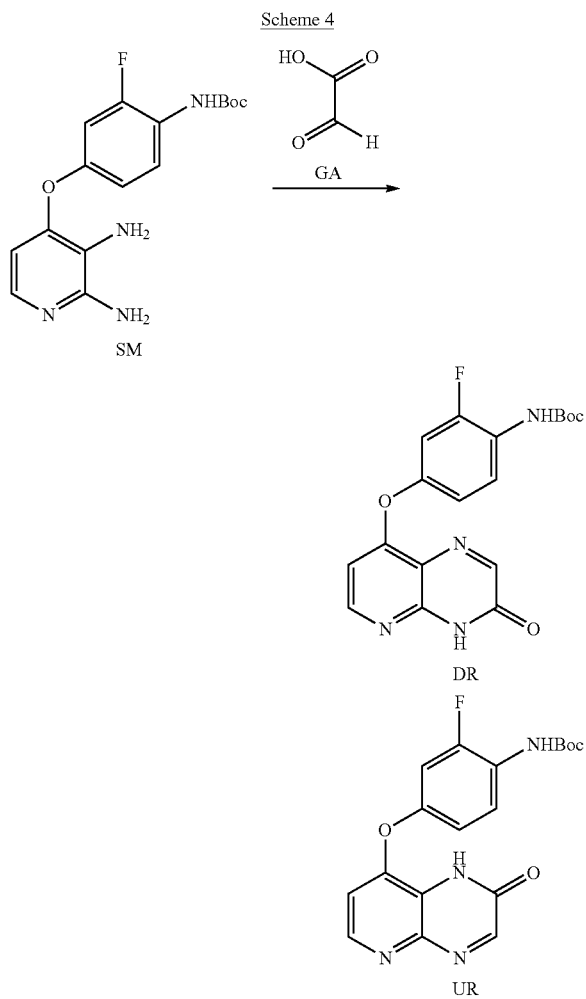

Reagent A: 500 mg of tert-butyl N-[4-[(2,3-diamino-4-pyridyl)oxy]-2-fluoro-phenyl]carbamate ("starting material", denoted SM) was dissolved in a solvent (denoted SM solvent), specifically, a volume (denoted SM solvent volume, SMSV) of the SM solvent. The mixture was warmed if necessary, and then allowed to cool to room temperature.

Reagent B: An amount of glyoxylic acid (denoted GA), handled as glyoxylic acid monohydrate, was provided. Either it was used as the solid (without solvent), or it was dissolved in the same solvent (i.e., the SM solvent), specifically, a volume (denoted GA solvent volume, GASV) of the SM solvent, and stirred at room temperature to provide a colourless solution.

In Studies 1-8, Reagent B was added to Reagent A over an addition time (denoted AT), while the resulting reaction mixture was maintained at a reaction temperature (denoted XT).

In Studies 9-34, Reagent A was added to Reagent B over an addition time (denoted AT), while the resulting reaction mixture was maintained at a reaction temperature (denoted XT).

The reaction mixture was then stirred overnight, and the proportions (molar %) of starting material (SM), desired regioisomer (DR), and undesired regioisomer (UR) in the resulting product was determined spectroscopically by HPLC (i.e., giving spectroscopic yields).

In this context, the solvent volume (i.e., the SM solvent volume and GA solvent volume) is reported in units of "volumes", where one "volume" is the numerical equivalent, in litres, of the weight of the starting material, SM, in kilograms. (In a sense, the solvent is treated as if it had a density of 1 g/cm$^3$, and 1 volume is that volume of solvent which has the same weight as the starting material, SM.) And so, in Study 7 described below, 500 mg (i.e., 0.5 g) of SM was dissolved in 25 volumes of SM solvent (i.e., 25×0.5 mL=12.5 mL) and 2 equivalents of glyoxylic acid monohydrate was dissolved in 1 volume of SM solvent (i.e., 1×0.5 mL=0.5 mL). Similarly, in Study 33 described below, 500 g (i.e., 0.5 kg) of SM was dissolved in 10 volumes of SM solvent (i.e., 10×0.5 L=5 L) and 10 equivalents of glyoxylic acid monohydrate was dissolved in 10 volumes of SM solvent (i.e., 10×0.5 L=5 L).

In these studies, the SM is tert-butyl N-[4-[(2,3-diamino-4-pyridyl)oxy]-2-fluoro-phenyl]carbamate, which has an empirical formula of $C_{16}H_{19}FN_4O_3$ and a molecular weight of 334.34 g/mol; consequently, one kilogram contains about 3 moles of SM. And so, in Study 7 described below, the theoretical concentration of SM in the reaction mixture is about 1.5 mmol in 13 mL, or about 0.115 M. Similarly, in Study 33 described below, the theoretical concentration of SM in the reaction mixture is about 1.5 mol in 10 L, or about 0.15 M.

| Study No. | SM solv. | SMSV (vol.) | GASV (vol.) | GA (eq.) | XT (° C.) | AT | Notes | SM % | DR % | UR % |
|---|---|---|---|---|---|---|---|---|---|---|
| 1 | MeOH | 25 | none | 2 | 20 | 30 sec | (a) | 4 | 43 | 52 |
| 2 | EtOH | 25 | none | 2 | 20 | 30 sec | (a) | 2 | 34 | 60 |
| 3 | THF | 25 | none | 2 | 20 | 30 sec | (a) | 5 | 25 | 66 |
| 4 | MeOH | 25 | none | 10 | 20 | 30 sec | (a) | 4 | 77 | 19 |
| 5 | EtOH | 25 | none | 10 | 20 | 30 sec | (a) | 3 | 55 | 40 |
| 6 | THF | 25 | none | 10 | 20 | 30 sec | (a) | <0.5 | 83 | 17 |
| 7 | MeOH | 25 | 1 | 2 | 65 | 30 sec | (a) | <0.5 | 35 | 63 |
| 8 | EtOH | 25 | 1 | 2 | 78 | 30 sec | (a) | <0.5 | 25 | 70 |
| 9 | MeOH | 10 | 10 | 5 | 20 | 30 min | | 3 | 66 | 31 |
| 10 | MeOH | 10 | 10 | 5 | 0 | 30 min | | <1 | 71 | 29 |
| 11 | MeOH | 10 | 10 | 5 | 60 | 30 min | | <1 | 60 | 40 |
| 12 | MeOH | 10 | 10 | 10 | 20 | 30 min | | 3 | 78 | 19 |
| 13 | MeOH | 10 | 10 | 10 | 20 | 30 min | (b) | <1 | 71 | 17 |
| 14 | MeOH | 10 | 10 | 2 | 65 | 30 min | | <1 | 35 | 63 |
| 15 | EtOH | 10 | 10 | 2 | 78 | 30 min | | <1 | 25 | 70 |
| 16 | MeOH | 10 | 10 | 10 | 20 | 30 min | (c) | 19 | 66 | 19 |
| 17 | MeOH | 4 | 4 | 10 | 20 | 30 min | | 11 | 70 | 18 |
| 18 | MeOH | 10 | 10 | 10 | 20 | 3 hr | | 3 | 87 | 10 |
| 19 | MeOH | 10 | 10 | 10 | 20 | 3 hr | (d) | <1 | 88 | 11 |
| 20 | MeOH | 8 | 2 | 10 | 20 | 3 hr | | 5 | 78 | 18 |

| Study No. | SM solv. | SMSV (vol.) | GASV (vol.) | GA (eq.) | XT (° C.) | AT | Notes | SM % | DR % | UR % |
|---|---|---|---|---|---|---|---|---|---|---|
| 21 | MeOH | 8 | 2 | 10 | 20 | 6 hr | | <1 | 74 | 25 |
| 22 | MeOH | 10 | 10 | 10 | 20 | 6 hr | | <1 | 89 | 10 |
| 23 | MeOH | 10 | 10 | 5 | 20 | 30 min | | 3 | 66 | 31 |
| 24 | MeOH | 10 | 10 | 5 | 0 | 30 min | | <1 | 71 | 29 |
| 25 | MeOH | 10 | 10 | 5 | 60 | 30 min | | <1 | 60 | 39 |
| 26 | MeOH | 10 | 10 | 2 | 20 | 2 hr | (e) | <1 | 26 | 72 |
| 27 | MeOH | 10 | 10 | 5 | 20 | 3 hr | (f) | <1 | 79 | 19 |
| 28 | MeOH | 10 | 10 | 2 | 20 | 2 hr | (g) | 79 | 10 | 9 |
| 29 | MeOH | 10 | 10 | 10 | 20 | 3 hr | (h) | <1 | 85 | 13 |
| 30 | MeOH | 15 | 10 | 10 | 20 | 3 hr | (h) | 1.6 | 83 | 14 |
| 31 | MeOH | 10 | 10 | 10 | 20 | 3 hr | (i) | 1 | 83 | 14 |
| 32 | MeOH | 10 | 10 | 10 | 20 | 4.5 hr | (h), (j) | <1 | 83 | 15 |
| 33 | MeOH | 10 | 10 | 10 | 20 | 6.5 hr | (h), (k) | <1 | 89 | 10 |
| 34 | MeOH | 10 | 10 | 10 | 20 | 6.0 hr | (h), (k) | <1 | 89 | 10 |

Legend and Notes:
SM = starting material.
GA = glyoxylic acid.
SMSV = starting material solvent volume.
GASV = glyoxylic acid solvent volume.
DR = desired regioisomer.
UR = undesired regioisomer.
XT = reaction temperature.
AT = addition time.
(a) Glyoxylic acid added in one portion over 30 seconds.
(b) Glyoxylic acid stripped out with EtOH (2 × 10 mL) to remove water.
(c) Anhydrous MgSO$_4$ (250 mg) added to remove water.
(d) MeOH was anhydrous MeOH.
(e) AcOH (10 eq.) also added.
(f) AcOH (5 eq.) also added.
(g) Concentrated H$_2$SO$_4$ (10 eq.) also added.
(h) MeOH was "drum" MeOH.
(i) Glyoxylic acid was oven-dried overnight before use.
(j) Performed on a larger scale, with 50 g of SM.
(k) Performed on a larger scale, with 500 g of SM.

Studies 1-8: The addition of glyoxylic acid in one portion gave an excellent ratio at room temperature, but the ratio became worse at reflux. However, this method of addition was not suitable for use at larger scales. The results also showed that a large excess of glyoxylic acid was required.

Studies 9-17: Performing the reaction at higher than ambient temperature led to a worse ratio. The reaction can be performed at 0° C., but this does not improve the profile. The use of MgSO$_4$ to remove water or using anhydrous MeOH made no difference.

Studies 20-25: MeOH was found to give a slightly better ratio, as compared to EtOH. Addition times of 3 to 6 hours at 20° C. using 10 equivalents of glyoxylic acid monohydrate in 20 volumes (total) of MeOH gave the best profile.

Studies 26-31: The HPLC results indicate that moisture in the reaction mixture is not detrimental. This is also demonstrated by the use of drum MeOH as compared to the more expensive HPLC MeOH and oven-drying the glyoxylic acid monohydrate (which is hygroscopic) prior to use, neither of which improved the profile. Efforts to reduce the equivalents of glyoxylic acid monohydrate from 10 to 5 with addition of another (e.g., cheaper) acid (AcOH or H$_2$SO$_4$) led to a worse regioisomer ratio.

Study 32: A further study on a larger scale (50 g), based on the conditions used in Study 22, gave a spectroscopic yield of 83%. Different work-ups of the product were then studied in separate runs to optimize the isolated yield (i.e., the yield after work-up and purification). Work-up 1: Concentration of the reaction mixture in vacuo and an EtOH recrystallisation (10 vols) gave a 48% yield. Work-up 2: Concentration of the reaction mixture in vacuo and a MeOH slurry (3 vols) gave a 64% yield. Work-up 3: Cooling of the reaction mixture to 0° C. for 1 hour before filtering gave a 60% yield. Work-up 4: Removal of approximately half the volume of MeOH in vacuo, cooling to 0° C. for 1° hour, and filtering gave a 69% yield; the product contained 1-2% wt/wt glyoxylic acid monohydrate (starting material), which was removed via a water slurry.

Studies 33-34: Two further studies on an even larger scale (500 g), based on the conditions used in Study 22, gave a spectroscopic yield of 89%. For Study 34, see also Synthesis 3 below, where an isolated yield of 67% was obtained.

Chemical Synthesis

The syntheses described below relate to tert-butyl N-[4-[(2,3-diamino-4-pyridyl)oxy]-2-fluoro-phenyl]carbamate. However, it is believed that same conditions can be applied to structurally similar analogs, as described herein (i.e., with corresponding groups —R$^1$, —R$^2$, and -NPG).

Synthesis 1 tert-Butyl N-[4-[(2-amino-3-nitro-4-pyridyl)oxy]-2-fluoro-phenyl]carbamate

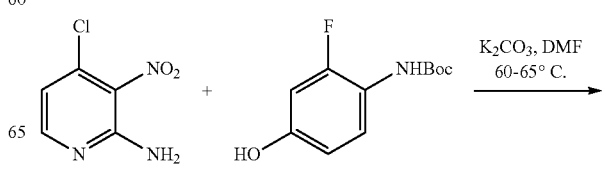

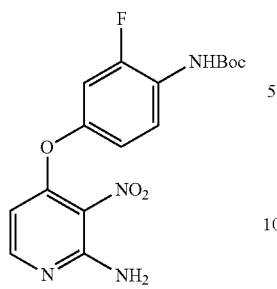

To a 50 L flange flask was charged tert-butyl (2-fluoro-4-hydroxyphenyl)carbamate (2840 g active, 12.50 mol) and dimethylformamide (DMF) (18.5 L) followed by 2-amino-3-nitro-4-chloropyridine (2083 g, 12.00 mol) and $K_2CO_3$ (2420 g, 17.51 mol). DMF (3.5 L) was used for washings. The mixture was heated at 60-65° C. for 5 hours (HPLC showed <2% starting material) before being allowed to cool to room temperature overnight. The batch was split into two halves, and to each half water (16 L) was added dropwise at <30° C. (exothermic addition) and the mixture stirred for 1 hour. The solids were filtered off, washed with water (2×5 L) and then oven dried at 60° C. to give 4100 g of the title compound as a dark solid (>95% by HPLC, >95% by NMR, 90% yield).

A total of 7127 g tert-butyl (2-fluoro-4-hydroxyphenyl)carbamate was processed which provided 10431 g tert-butyl (4-((2-amino-3-nitropyridin-4-yl)oxy)-2-fluorophenyl)carbamate (91% overall yield).

| Batch no. | Carbamate Reagent | Product | Yield |
|---|---|---|---|
| 1 | 2840 g active | 4100 g active | 90% |
| 2 | 2678 g active | 3828 g active | 89% |
| 3 | 1609 g active | 2503 g active | 97% |
| TOTAL | 7127 g active | 10431 g active | 91% |

Synthesis 2 tert-Butyl N-[4-[(2,3-diamino-4-pyridyl)oxy]-2-fluoro-phenyl]carbamate

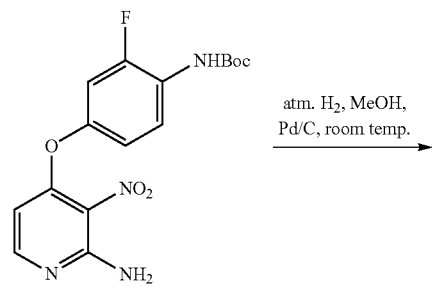

atm. $H_2$, MeOH, Pd/C, room temp.

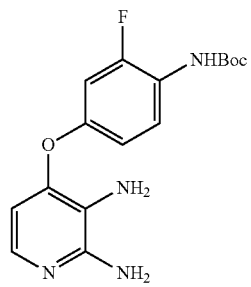

To a 50 L vessel was charged 5% Pd/C (128 g, 50% wet) and MeOH (23 L). tert-Butyl (4-((2-amino-3-nitropyridin-4-yl)oxy)-2-fluorophenyl)carbamate (2560 g, 7.03 mol) was charged followed by a MeOH wash (2.6 L). The slurry was stirred at 20-25° C. whilst gassing with $H_2$ (3 h) and then stirred overnight under an $H_2$ atmosphere. After this time, approximately 30% of the starting material remained, so additional 5% Pd/C (128 g, 50% wet) was charged, and the mixture sparged with $H_2$ for a further 4 hours. The reaction mixture was stirred overnight under an $H_2$ atmosphere and was complete by HPLC. The catalyst was filtered off and MeOH (5.7 L) used for washings. The filtrate was concentrated in vacuo, stripped with EtOH (5 L), and oven dried to give 2355 g of the title compound in 100% yield. Purity >95% by NMR and HPLC.

A total of 10431 g tert-butyl (4-((2-amino-3-nitropyridin-4-yl)oxy)-2-fluorophenyl)carbamate was processed, which provided 9478 g tert-butyl (4-((2,3-diaminopyridin-4-yl)oxy)-2-fluorophenyl)carbamate (99% overall yield).

| Batch no. | Nitro Reagent | Product | Yield |
|---|---|---|---|
| 1 | 2560 g active | 2355 g | 100% |
| 2 | 1540 g active | 1392 g | 98% |
| 3 | 6331 g active | 5731 g | 99% |
| TOTAL | 10431 g active | 9478 g | 99% |

Synthesis 3 tert-Butyl (2-fluoro-4-((3-oxo-3,4-dihydropyrido[2,3-b]pyrazin-8-yl)oxy)phenyl)carbamate

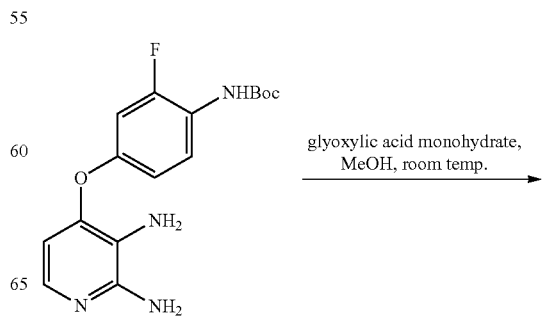

glyoxylic acid monohydrate, MeOH, room temp.

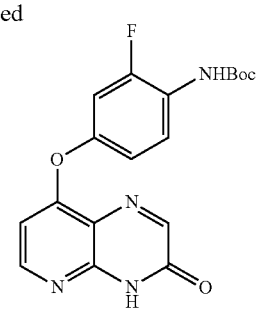

(As described above in Study 34.) To a 20 L flask was charged glyoxylic acid monohydrate (1376 g, 14.95 mol) and MeOH (5 L). The mixture was stirred at room temperature to provide a colourless solution. tert-Butyl N-[4-[(2,3-diamino-4-pyridyl)oxy]-2-fluoro-phenyl]carbamate (500 g, 1.495 mol) was dissolved in MeOH (5 L) via warming to 40° C. The solution was allowed to cool to room temperature and added dropwise to the reaction vessel over 6.5 hours at 18-22° C. (no exotherm observed) and the reaction mixture was then stirred overnight. HPLC (220 nm) showed 89% product, 10% regioisomer, <1% starting material. The reaction mixture was stripped to approximately one-half volume on a rotavapor at 40° C., before being cooled to 0° C. for 1 hour. The solids were filtered off, washed with cold MeOH (500 mL), and then water (500 mL) to remove any residual glyoxylic acid monohydrate. The solid was dried overnight in a vacuum oven at 45° C. to provide 414 g of the title compound in 74% yield (purity >97% by NMR, >99% by HPLC).

The product was combined with two crude batches of product obtained using 50 g and 500 g tert-butyl N-[4-[(2,3-diamino-4-pyridyl)oxy]-2-fluoro-phenyl]carbamate and adsorbed onto silica (1400 g). The material was purified by column chromatography on silica (4 kg) eluting with 30% THF/DCM (40 L) then 40% THF/DCM (40 L). The product fractions were combined and concentrated to give 906 g product. This was slurried in 1:1 Et$_2$O:heptane (8 L) for 1 hour at room temperature before being filtered off and washed with heptane (1 L). The material was oven dried to provide 842.2 g product, which contained ~7% solvent by NMR (5% THF, 2% DCM). Total active=783 g (67% yield). Purity >97% by NMR (excluding solvents) and >99% by HPLC.

In summary, a total of 1050 g tert-butyl N-[4-[(2,3-diamino-4-pyridyl)oxy]-2-fluoro-phenyl]carbamate was processed to give 783 g tert-butyl (2-fluoro-4-((3-oxo-3,4-dihydropyrido[2,3-b]pyrazin-8-yl)oxy)phenyl)carbamate in a 67% yield (following a silica plug column to remove baseline impurities).

Synthesis 4

8-(4-amino-3-fluoro-phenoxy)-4H-pyrido[2,3-b]pyrazin-3-one

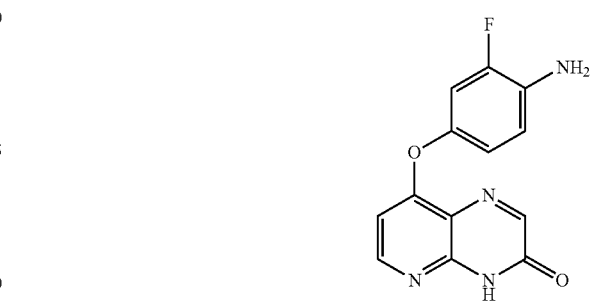

To a 10 L flask was charged tert-butyl (2-fluoro-4-((3-oxo-3,4-dihydropyrido[2,3-b]pyrazin-8-yl)oxy)phenyl)carbamate (783 g, 2.10 mol) and 1 M tetra-n-butylammonium fluoride (TBAF) in tetrahydrofuran (THF) (8.5 L, 8.5 mol). The mixture was heated to reflux and the temperature maintained for 30 hours. HPLC indicated the reaction was complete. The THF was removed in vacuo and MeOH (8 L) added to the crude black oil. The resulting slurry was stirred for 1 hour, filtered, and washed with MeOH (1 L). $^1$H NMR analysis showed approximately 11% TBAF was present; therefore, the material was re-slurried in MeOH (8 L) for 1 hour, filtered, and washed with MeOH (1 L). The product was dried at 45° C. overnight to afford 415 g of the title compound (NMR >95%, HPLC >97%, <1% TBAF by NMR, 72% yield).

A total of 2217 g tert-butyl (2-fluoro-4-((3-oxo-3,4-dihydropyrido[2,3-b]pyrazin-8-yl)oxy)phenyl)carbamate was deprotected using the TBAF method to provide 1208.5 g 8-(4-amino-3-fluorophenoxy)pyrido[2,3-b]pyrazin-3(4H)-one in 75% yield.

| Batch no. | Protected Reagent | Product | Yield |
|---|---|---|---|
| 1 | 783 g active | 415 g | 72% |
| 2 | 735 g active | 379.5 g | 71% |
| 3 | 699 g active | 414 g | 81% |
| TOTAL | 2217 g active | 1208.5 g | 75% |

Synthesis 5

5-tert-Butyl-2-(3-fluorophenyl)pyrazol-3-amine

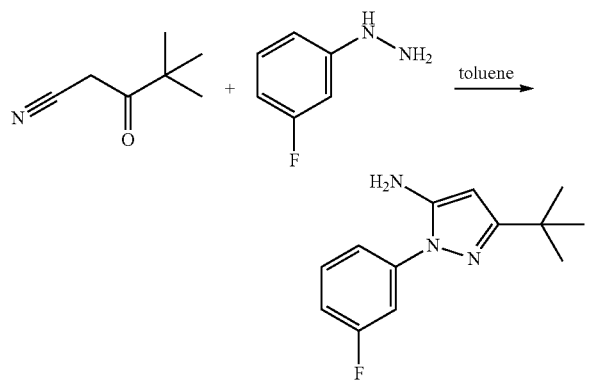

A mixture of 4,4-dimethyl-3-oxopentane nitrile (77 g, 0.62 mol) and 3-fluorophenylhydrazine hydrochloride (100 g, 0.62 mol) was added to toluene (1 L) and heated to 100° C. (reflux) for 24 hours. The reaction mixture was then allowed to cool to 20° C. The reaction mixture was then filtered, washed with toluene (2×250 mL), and dried in vacuo. The crude HCl salt was combined with a previous batch (performed using 180 g of 3-fluorophenylhydrazine hydrochloride) and partitioned between DCM (4 L) and sat. aq. NaHCO$_3$ (4 L). The mixture was stirred until no solid remained. The DCM layer was separated off, dried (MgSO$_4$), filtered, and concentrated in vacuo to provide the title compound as an orange solid (210 g) in 52% yield. Purity >95% by NMR and 94.4% by LCMS.

Synthesis 6

Phenyl N-[5-tert-butyl-2-(3-fluorophenyl)pyrazol-3-yl]carbamate

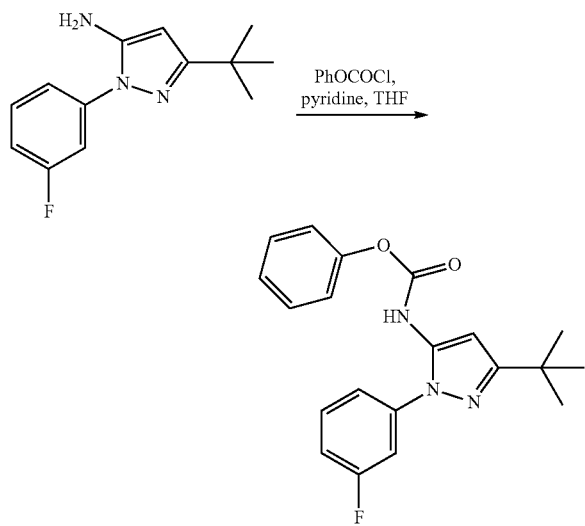

5-tert-Butyl-2-(3-fluorophenyl)pyrazol-3-amine (210 g, 0.90 mol) was dissolved in THF (5 L) at 0° C. before the addition of pyridine (146 mL, 1.80 mol). Phenyl chloroformate (113 mL, 0.90 mol) in THF (300 mL) was charged dropwise at 0-5° C. over 30 minutes. The reaction mixture was stirred at 0° C. for 30 minutes, and then allowed to warm to room temperature. After 4 hours, HPLC showed 8% stage 1 remained. A further charge of phenyl chloroformate (11 mL, 0.088 mol) was added, and after 30 minutes, HPLC analysis indicated the reaction was complete. EtOAc (5 L) was charged and the organic layer washed with 1 M HCl (2×1.2 L), water (1.2 L), sat. aq. NaHCO$_3$ (1.2 L) and sat. brine (1.2 L). The organic layer was dried (MgSO$_4$), filtered, and concentrated in vacuo. The crude oil was taken up in a 1:3 mixture of EtOAc:heptane and concentrated in vacuo to give a solid. The solid was slurried in heptane (2.5 L) for 1 hour, filtered, and washed with heptane (200 mL). The material was oven dried at 40° C. overnight to afford the title compound (286 g) in 90% yield. Purity >95% by NMR.

Synthesis 7

1-[2-Fluoro-4-[(3-oxo-4H-pyrido[2,3-b]pyrazin-8-yl)oxy]phenyl]-3-[2-(3-fluorophenyl)pyrazol-3-yl]urea

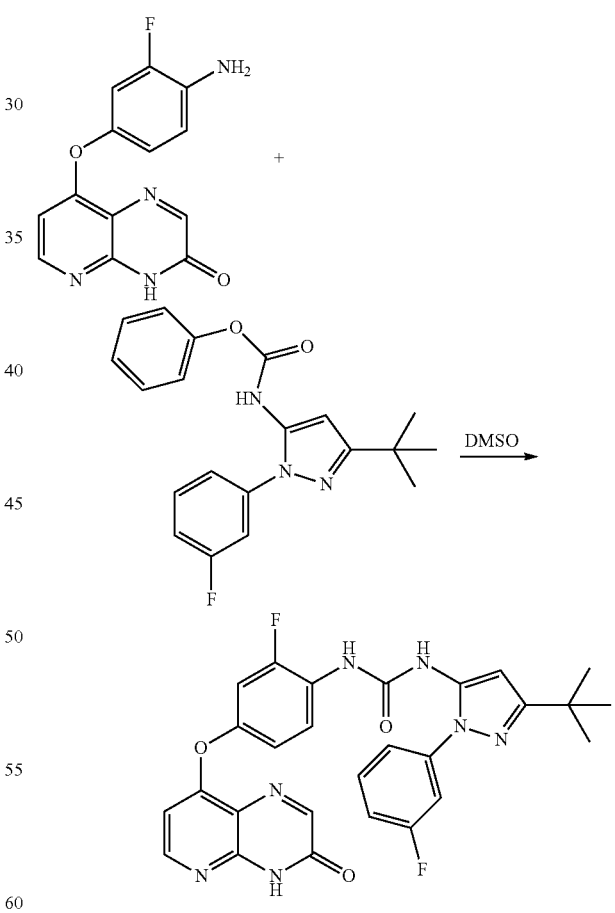

To 8-(4-amino-3-fluorophenoxy)pyrido[2,3-b]pyrazin-3(4H)-one (169.5 g, 0.623 mol) was charged phenyl N-[3-tert-butyl-1-(3-fluorophenyl)-1H-pyrazol-5-yl]carbamate (220 g, 0.623 mol) and DMSO (1.7 L). The reaction mixture was stirred at 20-22° C. overnight. $^1$H NMR indicated that the reaction was complete. The reaction mixture was quenched into water (8.6 L) and stirred for 1 hour before being filtered and washed with water (2×2 L). The material was oven dried at 60° C. over the weekend. The solid was slurried in EtOAc (3.39 L) for 1 hour, filtered, and washed with EtOAc (750 mL) to give 320 g of product. NMR indicated phenol was still present. The material was re-slurried in EtOAc (3.2 L) for 1 hour, filtered, and washed with EtOAc (500 mL) and dried to afford 293 g of the title compound (9% EtOAc by NMR, one single impurity 0.8%). The solid was recrystallised from THF (5.7 L) and heptane (2.85 L) as follows: THF was added and the mixture heated to reflux to achieve a solution. Heptane was then added over 40 minutes at 66° C. and the solution seeded at 60° C.; the batch was then allowed to cool to room temperature before filtering off the solids. The filter cake was washed with heptane (2.85 L) and oven dried at 45° C. overnight to give 211 g of title compound (64% yield).

Synthesis 8 tert-Butyl N-[4-[(3-oxo-4H-pyrido[2,3-b]pyrazin-8-yl)oxy)-1-naphthyl)carbamate

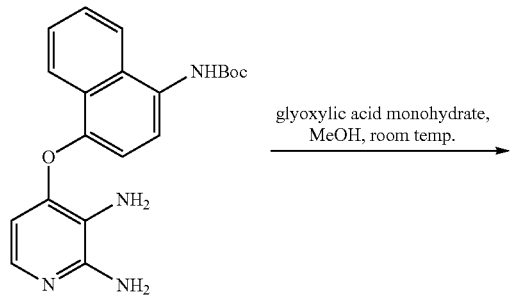

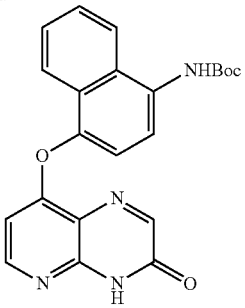

Glyoxylic acid monohydrate (2.75 g, 30 mmol) was dissolved in MeOH (10 mL). A solution of tert-butyl (4-((2,3-diaminopyridin-4-yl)oxy)naphthalen-1-yl)carbamate (1.1 g, 3 mmol) (for synthesis, see, e.g., Menard et al., 2009) in 25 mL MeOH was prepared by heating the flask until no more solid remained. This solution was added dropwise (slowly over 3 hours) to the stirred solution of glyoxylic acid. After stirring overnight, a precipitate was formed. The reaction mixture was concentrated and the solid recovered by filtration and washed with 10 mL cold MeOH, and then with water. The cake was dried to afford the desired regioisomer (according to NMR, as compared to reported literature compound), yield 627 mg (50%).

Comparison with Known Methods

As summarised below, the methods described herein provide a substantially improved yield, as compared to the known method, for example, an increase from 25% to 67-74% and an increase from 7% to 50%.

Comparison 1

|  |  | Desired Regioisomer | Undesired Regioisomer |
|---|---|---|---|
| Known method[1] | Spect. Yield | Not determined | Not determined |
|  | Isolated Yield | 25% | 69% |
| Present method[2] | Spect. Yield | 89% | 10% |
|  | Isolated Yield | 74%/67% | Not isolated |

(1): Zambon et al., 2010: To a solution of tert-butyl 4-(2,3-diaminopyridin-4-yloxy)-2-fluorophenylcarbamate (3.50 g, 10.5 mmol) in dry EtOH were added consecutively molecular sieves (3Å) and ethyl glyoxylate (3.6 mL of a 50% solution in toluene, 1.7 equivalents). The solution was stirred at room temperature for 3 hours until the starting material was consumed (monitored by TLC). The desired regioisomer was isolated to give 0.96 g product (25% yield).

(2): See Synthesis 3 above.

Comparison 2

| | | Desired Regioisomer | Undesired Regioisomer |
|---|---|---|---|
| Known method[3] | Spect. Yield | Not determined | Not determined |
| | Isolated Yield | 7% | 42% |
| Present method[4] | Spect. Yield | Not determined | Not determined |
| | Isolated Yield | 50% | Not isolated |

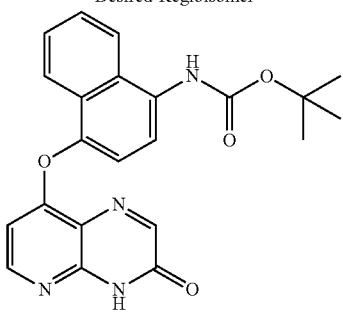

(3): Zambon et al., 2010: To a solution of tert-butyl 4-(2,3-diaminopyridin-4-yloxy)naphthalen-1-ylcarbamate (3.1 g, 8.2 mmol) in dry EtOH were added consecutively molecular sieves (3Å) and ethyl glyoxylate (2.8 mL of a 50% solution in toluene, 1.7 equivalents). The solution was stirred at room temperature for 3 hours until the starting material was consumed (monitored by TLC). The desired regioisomer was isolated by chromatography with 50% ethyl acetate, to give 0.24 g product (7% yield). (Note that there is an error in the publication; the reported yield of 240 mg corresponds to a 7% yield, not a 9% yield.)
(4): See Synthesis 8 above.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Abosolo et al., 1990, "Kinetic study on the anelation of heterocycles. 2. pyrido[2,3-b]pyrazine and pyrido[3,4-b] pyrazine derivatives synthesized by the hinsberg reaction", J. Heterocyclic Chem., Vol. 27, No. 2, pp. 157-162.

Ballell et al., 2008, "Derivatives and analogs of N-ethylquinolines and N-ethylazaquinolones", international (PCT) patent application publication number WO 2008/009700 A1, published 24 Jan. 2008.

Bates et al., 1990, "A New Synthesis of Pyrazino[2,3-c] isoquinolines", Australian J. Chem., Vol. 43, No. 1, pp. 179-184.

Bekerman, 1992, "Comparative Kinetic Studies on the Synthesis of. Quinoxalinone Derivatives and Pyrido[2,3-b] pyrazinone. Derivatives by the Hinsberg Reaction", J. Heterocyclic Chem., Vol. 29, No. 1, pp. 129-133.

Bergman et al., 1996, "Synthesis of pyridopyrazino[2,3-b] indoles and 10H-indolo[3,2-g]pteridins", Recueil des Travaux Chimiques des Pays-Bas, Vol. 115, No. 1, pp. 31-36.

Clark-Lewis et al., 1957, "Quinoxaline derivatives. Part IV. Dihydro-oxo-1:4:5-triazanaphthalenecarboxyureides and related spirohydantoins", J. Chem. Soc., pp. 430-437.

Cushman et al., 1992, "$^{19}$F NMR Studies on the Mechanism of Riboflavin Synthase. Synthesis of 6-(Trifluoromethyl)-7-oxo-8-(D-ribityl)lumazine and 6-(Trifluoromethyl)-7-methyl-8-(D-ribityl)lumazine", J. Org. Chem., Vol. 57, No. 21, pp. 5630-5643.

Dettner et al., 1996, "Chemical defense of giant springtail Tetrodontophora bielanensis (Waga) (Insecta: Collembola)", J. Chem. Ecology, Vol. 22, No. 5, pp. 1051-1074.

Dubey et al., 2001, "Structure and reactions of monoanils obtained from 2,3-pyridinediamines", Indian J. Chem, Section B, Org. Chem. including Med. Chem., Vol. 40, No. 5, pp. 361-367.

Hoekstra et al., 2012, "Metalloenzyme inhibitor compounds", international (PCT) patent application publication number WO 2012/177725 A1, published 27 Dec. 2012.

Leese et al., 1955, "Polyazanaphthalenes. Part I. Some derivatives of 1:4:5-triazanaphthalene and quinoxaline", J. Chem. Soc., pp. 303-309.

Mashelkar et al., 2006, "Synthesis of some novel 4-substituted coumarins having potential biological activity (Part II)", Indian J. Chem., Section B, Org. Chem. including Med. Chem., Vol. 45, No. 4, pp. 967-971.

McKillop et al., 1997, "Applications of Ethyl Carboethoxy-formimidate to Heterocyclic Synthesis: Preparation of Condensed Pyrazinones and 1,4-Oxazinones", Synthesis, No. 3, pp. 301-304.

Menard et al., 2009, "Novel Potent BRAF Inhibitors: Toward 1 nM Compounds through Optimization of the Central Phenyl Ring", J. Med. Chem., Vol. 52, No. 13, pp. 3881-3891.

Milbank et al., 2011, "Hepatis C virus inhibitors", international (PCT) patent application publication number WO 2011/004276 A1, published 13 Jan. 2011.

Murray et al., 2011, "Respiratory formulations and compounds for use therein", international (PCT) patent application publication number WO 2011/158044 A2, published 22 Dec. 2011.

Properties of BRAF Inhibitors", J. Med. Chem., Vol. 53, pp. 5639-5655.

Reck et al., 2011, "Novel N-Linked Aminopiperidine Inhibitors of Bacterial Topoisomerase Type II: Broad-Spectrum Antibacterial Agents with Reduced hERG Activity", *J. Med. Chem.*, Vol. 54, No. 22, pp. 7834-7847.

Remli et al., 1989, "Reaction of o-arylenediamines with ethyl 3-fluoro 2-ketoesters synthesis of quinoxaline derivatives", *J. Fluorine Chem.*, Vol. 44, pp. 15-24.

Rudy et al., 1938, "Zweikernige Alloxan-Abkommlinge von 2.3-Diamino-pyridinen", *Chemische Berichte*, Vol. 71, pp. 1323-1330.

Saari et al., 1978, "3-(1-Piperazinyl)-pyrido[2,3-b]pyrazines", U.S. Pat. No. 4,082,845 granted 4 Apr. 1978.

Seki et al., 1995, "Reaction products of dialkyl acetylenedicarboxylates with 2,3-diaminopyridine", *J. Heterocyclic Chem.*, Vol. 32, No. 3, pp. 1071-1074.

Sherman et al., 2007, "Synthesis of unsymmetrical and regio-defined 2,3,6-quinoxaline and 2,3,7-pyridopyrazine derivatives", *Tetrahedron Letters*, Vol. 48, No. 51, pp. 8943-8946.

Springer et al., 2009, "Pyrido[2,3-b]pyrazine-8-substituted compounds and their use", international (PCT) patent application publication number WO 2009/077766 A1, published 25 Jun. 2009.

Zambon et al., 2010, "Novel Hinge Binder Improves Activity and Pharmacokinetic Activity and Pharmacokinetic Properties of BRAF Inhibitors", *J. Med. Chem.*, Vol. 53, pp. 5639-5655.

Ziegler et al., 1949, "Some 9-Aza-alloxazines", *J. Am. Chem. Soc.*, Vol. 71, pp. 1891-1893.

The invention claimed is:

1. A method of preparing a compound of Formula (3):

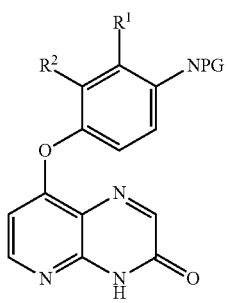

(3)

comprising the step of reacting a compound of Formula (1):

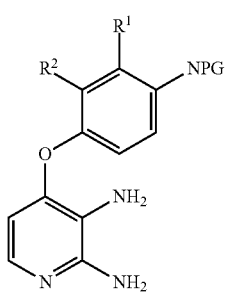

(1)

with a compound of Formula (2):

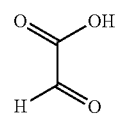

(2)

in a reaction mixture under cyclisation conditions to form said compound of Formula (3);
wherein the ratio of the amount of the compound of Formula (2) to the amount of the compound of Formula (1), on a molar basis, is at least about 2; and
wherein:
—$R^1$ is independently —H or —$R^{1A}$;
—$R^2$ is independently —H or —$R^{2A}$;
—$R^{1A}$ is independently —F, —Cl, —Br, —I, —$R^X$, —OH, —$OR^X$, or —$SR^X$;
—$R^{2A}$ is independently —F, —Cl, —Br, —I, —$R^X$, —OH, —$OR^X$, —$SR^X$;
each —$R^X$ is independently linear or branched saturated $C_{1-4}$alkyl;
or —$R^1$ and —$R_2$ together form —CH=CH—CH=CH—, —N=CH—CH=CH—, —CH=N—CH=CH—, —CH=CH—N=CH—, or —CH=CH—CH=N—; and
—NPG is a protected amino group which is stable to said cyclisation conditions.

2. The method according to claim 1, wherein —$R^1$ is —H.

3. The method according to claim 1, wherein —$R^1$ is —$R^{1A}$.

4. The method according to claim 1, wherein —$R^2$ is —H.

5. The method according to claim 1, wherein —$R^2$ is —$R^{2A}$.

6. The method according to claim 1, wherein —$R^{1A}$, if present, is independently —F, —Cl, —Br, or —I.

7. The method according to claim 1, wherein —$R^{1A}$, if present, is —F.

8. The method according to claim 1, wherein —$R^{1A}$, if present, is —OH.

9. The method according to claim 1, wherein —$R^{1A}$, if present, is —$OR^X$.

10. The method according to claim 1, wherein —$R^{1A}$, if present, is —$SR^X$.

11. The method according to claim 1, wherein —$R^{2A}$, if present, is
independently —F, —Cl, —Br, or —I.

12. The method according to claim 1, wherein —$R^{2A}$, if present, is —F.

13. The method according to claim 1, wherein —$R^{2A}$, if present, is —OH.

14. The method according to claim 1, wherein —$R^{2A}$, if present, is —$OR^X$.

15. The method according to claim 1, wherein —$R^{2A}$, if present, is —$SR^X$.

16. The method according to claim 1, wherein each —$R^X$, if present, is —Me.

17. The method according to claim 1, wherein —$R^1$ and —$R_2$ together form —CH=CH—CH=CH—, —N=CH—CH=CH —, —CH=N—CH=CH—, or —CH=CH—CH=N—.

18. The method according to claim 1, wherein —$R^1$ and —$R_2$ together form —CH=CH—CH=CH—.

19. The method according to claim 1, wherein —NPG is independently a protected amino group in the form of: a carbamate; an amide; an imide; or a sulfonamide.

20. The method according to claim 1, wherein —NPG is a protected amino group in the form of a carbamate.

21. The method according to claim 1, wherein —NPG is tert-butyl carbamate.

22. The method according to claim 1, wherein —NPG is a protected amino group in the form of an amide.

23. The method according to claim 1, wherein —NPG is a protected amino group in the form of an imide.

24. The method according to claim 1, wherein —NPG is a protected amino group in the form of a sulfonamide.

25. The method according to claim 1, wherein the ratio of the amount of the compound of Formula (2) to the amount of the compound of Formula (1), on a molar basis, is from about 2 to about 25.

26. The method according to claim 25, wherein said ratio is from about 2 to about 20.

27. The method according to claim 25, wherein said ratio is from about 2 to about 10.

28. The method according to claim 25, wherein said ratio is from about 5 to about 15.

29. The method according to claim 25, wherein said ratio is from about 5 to about 10.

30. The method according to claim wherein said ratio is about 10.

31. The method according to claim 1, wherein the compound of Formula (1) and the compound of Formula (2) are combined over an addition time of at least about 30 minutes to form the reaction mixture.

32. The method according to claim 31, wherein the addition time is from about 30 minutes to about 24 hours.

33. The method according to claim 31, wherein the addition time is from about 1 hour to about 18 hours.

34. The method according to claim 31, wherein the addition time is from about 2 hours to about 12 hours.

35. The method according to claim 31, wherein the addition time is from about 3 hours to about 6 hours.

36. The method according to claim 1, wherein, after the compound of Formula (1) and the compound of Formula (2) have been combined, the reaction is allowed to continue for a further reaction time.

37. The method according to claim 36, wherein the further reaction time is from about 1 hour to about 48 hours.

38. The method according to claim 36, wherein the further reaction time is from about 3 hours to about 24 hours.

39. The method according to claim 36, wherein, the reaction mixture is stirred during the further reaction time.

40. The method according to claim 1, wherein the reaction mixture further comprises a reaction solvent.

41. The method according to claim 40, wherein the reaction solvent is, or comprises, an organic solvent.

42. The method according to claim 40, wherein the reaction solvent is, or comprises, an alcohol, a linear or branched ether, a cyclic ether, or a mixture thereof.

43. The method according to claim 40, wherein the reaction solvent is, or comprises, an alcohol.

44. The method according to claim 40, wherein the reaction solvent is, or comprises, a $C_{1-4}$alkyl alcohol, or a mixture of two or more $C_{1-4}$alkyl alcohols.

45. The method according to claim 40, wherein the reaction solvent is MeOH, EtOH, or THF, or a mixture thereof.

46. The method according to claim 40, wherein the reaction solvent is MeOH, EtOH, or a mixture of MeOH and EtOH.

47. The method according to claim 40, wherein the reaction solvent is MeOH.

48. The method according to claim 40, Therein the volume of reaction solvent in the reaction mixture is from about 5 to about 50 L per kg of compound of Formula (1).

49. The method according to claim 48, wherein the volume of reaction solvent in the reaction mixture is from about 10 to about 30 L per kg of compound of Formula (1).

50. The method according to claim 48, Wherein the volume of reaction solvent in the reaction mixture is from about 15 to about 25 L per kg of compound of Formula (1).

51. The method according to claim 48, Wherein the volume of reaction solvent in the reaction mixture is about 20 L per kg of compound of Formula (1).

52. The method according to claim 40, wherein the concentration of the compound of Formula (1) in the reaction mixture, based on the amount of compound of Formula (1) and the amount of solvent used to form the reaction mixture, is from about 0.01 to about 1 M.

53. The method according to claim 52, wherein. said concentration is from about 0.02 to about 0.5 M.

54. The method according to claim 52, wherein said concentration is from about 0.05 to about 0.3 M.

55. The method according to claim 52, wherein said concentration is from about 0.05 to about 0.2 M.

56. The method according to claim 52, wherein said concentration is about 0.10 M.

57. The method according to claim 52, wherein said concentration is about 0.15 M.

58. The method according to claim 40, wherein the compound of Formula (1) is dissolved in a first solvent to form a starting material solution before being combined with the compound of Formula (2) to form the reaction mixture, wherein said first solvent is, or forms part of; the reaction solvent.

59. The method according to claim 40, wherein the compound of Formula (2) is dissolved in a second solvent to form a glyoxylic acid reagent solution before being combined with the compound of Formula (1) to form the reaction mixture, wherein said first solvent is, or forms part of, the reaction solvent.

60. The method according to claim 40, wherein:
the compound of Formula (1) is dissolved in a first solvent to form a starting material solution before being combined with the compound of Formula (2) to form the reaction mixture, wherein said first solvent forms part of the reaction solvent; and
the compound of Formula (2) is dissolved in a second solvent to form a glyoxylic acid reagent solution before being combined with the compound of Formula (1) to form the reaction mixture, wherein said second solvent forms part of the reaction solvent.

61. The method according to claim 60, wherein the first solvent and the second solvent are the same.

62. The method according to claim 60, wherein the first solvent and the second solvent are different.

63. The method according to claim 60, wherein said starting material solution is combined with said glyoxylic acid reagent solution by adding said starting material solution to said glyoxylic acid reagent solution.

64. The method according to claim 60, wherein said starting material solution is combined with said glyoxylic acid reagent solution by adding said glyoxylic acid reagent solution to said starting material solution.

65. The method according to claim 63, wherein said adding is adding continuously (e.g., over the addition time).

66. The method according to claim 65, wherein said adding continuously is adding by dropwise addition.

67. The method according to claim 65, wherein said adding continuously is adding by continuous flow addition.

68. The method according to claim 58, wherein the compound of Formula (2) is added as a solid to said starting material solution.

69. The method according to claim 58, wherein the compound of Formula (2) is added as a solid to said starting material solution continuously (e.g., over the addition time).

70. The method according to claim 59, wherein the compound of Formula (1) is added as a solid to said glyoxylic acid reagent solution.

71. The method according to claim 59, wherein the compound of Formula (1) is added as a solid to said glyoxylic acid reagent solution continuously (e.g., over the addition time).

72. The method according to claim 1, wherein the temperature of the reaction mixture during the reaction is, or is maintained at, a temperature of from about 0° C. to about the reflux temperature of the reaction mixture.

73. The method according to claim 72, wherein the temperature range is from about 0° C. to about 30° C.

74. The method according to claim 72, wherein the temperature range is from about 10° C. to about 30° C.

75. The method according to claim 72, wherein the temperature range is from about 15° C. to about 25° C.

76. The method according to claim 72, wherein the temperature is about 20° C.

77. The Method according to claim 1, further comprising a subsequent step of deprotecting said compound of Formula (3):

[Structure of Formula (3)]

to give a compound of Formula (4):

[Structure of Formula (4)]

78. The method according to claim 77, further comprising a subsequent step of reacting said compound of Formula (4):

[Structure of Formula (4)]

with a compound of Formula (5):

[Structure of Formula (5)]

to give a compound of Formula (6):

[Structure of Formula (6)]

wherein:
  -A is an activating group suitable for reaction with —$NH_2$ to form a urea group; and
  —Ar is phenyl, pyridyl, or naphthyl, and is optionally substituted with one or more groups —Y, wherein each —Y is independently selected from halo; linear or branched saturated $C_{1-4}$alkyl; linear or branched saturated $C_{1-4}$haloalkyl; —OH; linear or branched saturated $C_{1-4}$alkoxy; and linear or branched saturated $C_{1-4}$haloalkoxy.

79. The method according to claim 77, further comprising a subsequent step of activating said compound of Formula (4):

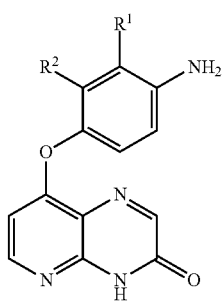

(4)

to give a compound of Formula (7):

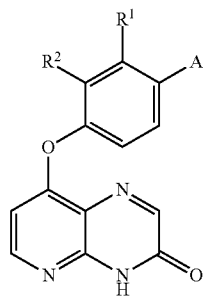

(7)

and the reacting the compound of Formula (7) with a compound of Formula (8):

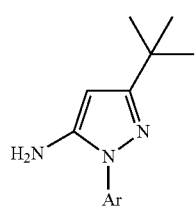

(8)

to give a compound of Formula (6):

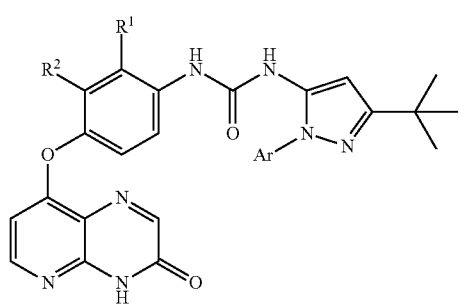

(6)

wherein:
-A is an activating group suitable for reaction with —NH₂ to form a urea group; and
—Ar is phenyl, pyridyl, or naphthyl, and is optionally substituted with one or more goups —Y, wherein each —Y is independently selected from halo; linear or branched saturated $C_{1-4}$alkyl; linear or branched saturated $C_{1-4}$ haloalkyl; —OH; linear or branched saturated $C_{1-4}$alkoxy; and linear or branched saturated $C_{1-4}$haloalkoxy.

80. The method according to claim 1, further comprising a preceding step of reducing a compound of Formula (7):

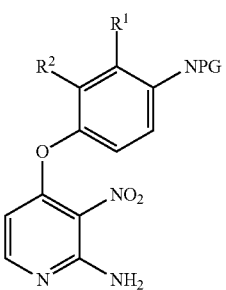

(7)

to give said compound of Formula (1):

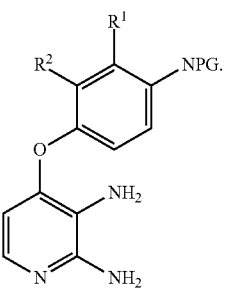

(1)

81. The method according to claim 80, further comprising preceding step of reacting a compound of Formula (8):

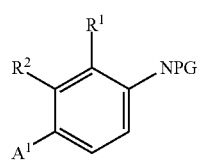

(8)

with a compound of Formula (9):

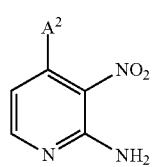

(9)

to give said compound of Formula (7):

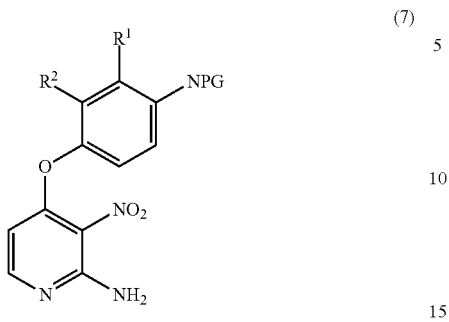

wherein -A¹ and -A² are activating groups suitable for reaction with each other to form an ether group.

82. The method according to claim 78, wherein each —Y is independently selected from the group consisting of —F, —Cl, —Br, —I, —Me, —Et, —CF$_3$, —OMe, —OEt, and —OCF$_3$.

83. The method according to claim 79, wherein each —Y is independently selected from the group consisting of —F, —Cl, —Me, —Et, —CF$_3$—OMe, —OEt, and —OCF$_3$.

* * * * *